US007811786B1

(12) United States Patent
Lee et al.

(10) Patent No.: US 7,811,786 B1
(45) Date of Patent: Oct. 12, 2010

(54) PREPARATION METHOD FOR THE PRODUCTION OF ACTIVE AND SOLUBLE PROTEINS IN PROKARYOTES AND POLYCISTRONIC VECTORS THEREFOR

(75) Inventors: Bong Yong Lee, Gyeonggi-do (KR); Seung Kook Park, Gyeonggi-do (KR); Shin Hye Park, Seoul (KR); Oh Byung Kwon, Gyeonggi-do (KR); Chae Ha Yoon, Gyeonggi-do (KR); Young Ju Kim, Busan (KR); Song Young Kim, Gyeonggi-do (KR); Kyung Hyun Min, Gyeonggi-do (KR); Yoon Seok Lee, Gyeonggi-do (KR); Tae Hee Lee, Gyeongsangbuk-do (KR); Tai Young Koo, Gyeonggi-do (KR)

(73) Assignee: Daewoong Co., Ltd., Gyunggi-Do (KR)

( * ) Notice: Subject to any disclaimer, the term of this patent is extended or adjusted under 35 U.S.C. 154(b) by 0 days.

(21) Appl. No.: 11/579,753

(22) PCT Filed: Jun. 11, 2004

(86) PCT No.: PCT/KR2004/001393

§ 371 (c)(1),
(2), (4) Date: Jun. 24, 2008

(87) PCT Pub. No.: WO2005/108585

PCT Pub. Date: Nov. 17, 2005

(30) Foreign Application Priority Data

May 6, 2004 (KR) ...................... 10-2004-0031977

(51) Int. Cl.
C12N 15/00 (2006.01)
C12N 1/20 (2006.01)
C12P 21/06 (2006.01)
(52) U.S. Cl. ................. 435/69.1; 435/252.3; 435/320.1
(58) Field of Classification Search .............. 435/252.3, 435/320.1, 69.2
See application file for complete search history.

(56) References Cited

U.S. PATENT DOCUMENTS

| 5,238,820 | A | 8/1993 | Kaufman |
| 5,648,254 | A | 7/1997 | Mulvihill et al. |
| 6,027,888 | A | 2/2000 | Georgiou et al. |
| 7,276,355 | B2 | 10/2007 | Furutani et al. |

FOREIGN PATENT DOCUMENTS

| KR | 100203919 B1 | 3/1999 |
| KR | 100254063 B1 | 4/2000 |
| KR | 20040007892 A | 1/2004 |

| WO | WO9814591 A1 | 4/1998 |
| WO | WO 02/072847 | 9/2002 |

OTHER PUBLICATIONS

Tran Van Nhieu et al., J. Bacteriology, 1987, 169(12), 5708-5714.*
English Translation of Abstract; Korean Publication No. KR100254063(B1); Applicant: Hanil Synthetics Inc., Published Apr. 15, 2000.
Jeffrey G. Thomas et al, "Molecular Chaperones, Folding Catalysts, and the Recovery of Active Recombinant Proteins from *E. coli*," (1997), Applied Biochemistry and Biotechnology 66, 197-238.
Andrew D. Guise, Shauna M. West, and Julian B. Chaudhuri "Protein Folding In Vivo and Renaturation of Recombinant Proteins from Inclusion Bodies," (1996), Molecular Biotechnology 6, 53-64.
English Translation of Abstract; Korean Publication No. KR20040007892(A); Applicant: Bioprogen Co. Ltd., Published Jan. 28, 2004 (1 pg.).
Schein, C. H. And M. H. M. Noteborn "Formation of Soluble Recombinant Proteins in *Escherichia coli* is Favored by Lower GROwrN Temperature," (1988), Biotechnology 6, 291-294.
Moore, J. T., Uppal, F. Maley and G. F. Maley "Overcoming Inclusion Body Formation in a High-Level Expression System," (1993), Protein. Expr. Purif. 4, 160-163.
Hartl, F. U., R. Holdan and T. Langer "Molecular chaperones in protein folding: the art of avoiding sticky situations," (1994), Trends Biochem. Sci. 19, 20-2.
Creighton, T. E., A. Zapun and N. J. Darby "Mechanisms and catalysts of disulphide bond formation in proteins," (1995), TIBTECH. 13, 18-27.
Gottesman, M. E. and W. A. Hendrickson "Protein folding and unfolding by *Escherichia coli* chaperones and chaperonins," 2000. Curr. Opin. Microbiol. 3, 197-202.
Smith, D. B. and Johnson, K. S. "Single-step purification of polypeptides expressed in *Escherichia coli* as fusions with glutathione S-transferase," (1988), Gene 67, 31-40.
Bedouelle, H. and Duplay, P. "Production in *Escherichia coli* and one-step purification of bifunctional hybrid proteins which bind maltose Export of the Klenow polymerase into the periplasmic space" (1988), Euro. J. Biochem. 171, 541-549.
Nilsson B. et al. "A synthetic IgG-binding domain based on staphylococcal protein A," (1987), Prot. Eng. 1, 107-113.
Savvas C. Makrides "Strategies for achieving high-level expression of genes in *Escherichia coli*," Microbiological Review, (1996), 512-538.
Studier FW et al. "Use of T7 RNA Polymerase to Direct Expression of Cloned Genes," Method Enzymol. (1990), 185, 60-89.
English Translation of Abstract; Korean Publication No. KR1020030065574; Applicant: Sekisui Chemical Co., Ltd; Published Jun. 8, 2003 (Abstract Only) (1 Pg).
English Translation of Abstract; Korean Publication No. KR100203919; Applicant: Hanil Synthetics Inc.; Published Mar. 25, 1999 (Abstract Only) (1 Pg).

* cited by examiner

*Primary Examiner*—Maryam Monshipouri
(74) *Attorney, Agent, or Firm*—Casimir Jones, S.C.

(57) ABSTRACT

Disclosed are a method of producing a target protein in a biologically-active, soluble form in prokaryotic cells and polycistronic vectors therefor.

18 Claims, 13 Drawing Sheets

US 7,811,786 B1

PREPARATION METHOD FOR THE PRODUCTION OF ACTIVE AND SOLUBLE PROTEINS IN PROKARYOTES AND POLYCISTRONIC VECTORS THEREFOR

This application is National Stage entry of PCT/KR04/01393, filed Jun. 11, 2004, which claims foreign priority to Korean application No. 10-2002-0031977, filed May 6, 2004.

TECHNICAL FIELD

The present invention relates to a method of producing a target protein in biologically-active, soluble forms in prokaryotes, and polycistronic vectors therefor.

BACKGROUND ART

The production system of heterogeneous proteins using recombinant *E. coli* ensures rapid cellular growth rates and high density cultures using inexpensive substrates and uses relatively well-identified genes in comparison with cases using other organisms, thereby making it possible to design various vector systems for facilitating the high expression and purification of heterogeneous proteins (Jeffrey G. T. and Amanda A. et al, (1997), *Applied Biochemistry and Biotechnology* 66, 197-238).

However, when *E. coli* is used as a host cell for the production of eukaryotic proteins, *E. coli* cannot perform post-translational modification such as glycosylation because it does not possess intracellular factors required for protein maturation. In addition, when a heterogeneous protein is expressed in high levels, it is often accumulated in the form of inclusion bodies, which are insoluble precipitates.

Inclusion bodies are typically formed by interaction between hydrophobic surfaces of folding intermediates of a target protein due to imbalance between the production rate and the folding rate of the target protein. In this case, inclusion bodies may be easily isolated, be typically less affected by proteinases and be accumulated in high concentrations in cells, thereby securing high yields and easy isolation of a target protein. Due to these advantages, the strategy of expressing a protein as inclusion bodies is utilized in the production of proteins unfavorable for in vivo folding. However, a target protein expressed as inclusion bodies requires an additional refolding process to recover its biological activity. The refolding of a target protein to an active form is dependent on experience, and is thus always not successful and makes it difficult to scale up the production of recombinant proteins in industrial scales. In addition, high molecular weight antibody proteins, tissue plasminogen activator (tPA) and factor VIII are very difficult to produce in active forms by a refolding process.

As described above, since inclusion body proteins should be refolded to have their structure and biological activity intact (Andrew D. Guise, Shauna M. West, and Julian B. Chaudhuri (1996), *Molecular Biotechnology* 6, 53-64), a target protein is expressed as a soluble protein using the so-called "in vivo protein folding technique" to induce its correct three-dimensional structure formation in vivo. Since this technique improves problems caused when a heterogeneous protein is expressed as inclusion bodies, it has an industrial importance in producing heterogeneous proteins in *E. coli*.

The following three strategies are typically used for in vivo folding of proteins.

The first strategy involves the control of protein expression sites and culture environments. When a target protein is designed to be expressed in the cytoplasm, although the target protein is harmful to cells, the cells are not damaged, and the protein is mostly expressed in very high levels. Also, this method facilities the preparation of expression vectors. As another method, the secretion of a target protein to the periplasm has advantages of simplifying protein purification and, compared to the method of expressing a protein in the cytoplasm, reducing protein degradation by proteinases and making disulfide bonding possible to some degree due to a relatively oxidative environment. The advantages further include that an authentic protein can be obtained by removing an N-terminal secretory signal. However, a secreted protein may be aggregated, resulting in formation of inclusion bodies, and reduced folding may occur. In a further method, the secretion of a target protein to culture media may solve the problems associated with protein folding and degradation by proteinases. However, *E. coli* rarely secretes proteins to culture media, and, even when proteins are secreted to media, proteins are greatly diluted, thus making purification rather difficult. This method is effective only in particular proteins and is thus not a generalized method to prevent inclusion bodies from being formed. Also, the fermentation control is frequently used to increase a soluble protein, and, in most cases, is the most economical method (Korean Pat. Application No. 1997-50023). The reduction of culture temperature is not applied to all proteins, but is a very effective method in many cases because it typically leads to decrease the production rate of a protein below the folding rate of the protein, resulting in no accumulation of folding intermediates with strong aggregation to each other (Schein, C. H. and M. H. M. Noteborn (1988), *Biotechnology* 6, 291-294; More, J. T., Uppal, F. Maley and G. F. Maley (1993), *Protein. Expr. Purif.* 4, 160-163).

The second strategy involves the co-expression of chaperones and protein foldases. The chaperones refer to proteins that function to help formation of the desired three-dimensional structure of protein and prevent unnecessary intermolecular or intramolecular interactions. Chaperone proteins derived from *E. coli* include GroEL, GroES, DnaK, HtpG, SecB and PapD, which protect folding intermediates and prevent aggregation and precipitation, and all of the *E. coli* chaperone proteins except for PapD (present in the periplasmic membrane) are present in the cytoplasm (Korean Pat. Application No. 2003-7008657; Hartl, F. U., R. Holdan and T. Langer (1994), *Trends Biochem. Sci.* 19, 20-25; Bernadea-Clark, E. and G. Georgiou (1994), *American Chem. Soc. Symp. Ser. Vol.* 470, ACS). Foldases refer to an auxiliary protein family that serves to facilitate covalent boding or isomerization during folding. Enzymes stimulating the disulfide bond formation of proteins include DsbA, DsbB, DsbC and DsbD (Creighton, T. E., A. Zapun and N. J. Darby (1995), *TIBTECH.* 13, 18-27; Gottesman, M. E. and W. A. Hendrickson (2000. *Curr. Opin. Microbiol.* 3, 197-202).

The third strategy involves the use of fusion proteins. Many proteins have been developed as fusion proteins, which include glutathione-S-transferase, maltose-binding protein, Protein A, tumor necrosis factor-α and lysyl-tRNA synthetase (Smith, D. B. and Johnson, K. S. (1988), *Gene* 67, 31-40.; Bedouelle, H. and Duplay, P. (1988), *Euro. J. Biochem.* 171, 541-549.; Nisson, B. et al. (1987), *Prot. Eng.* 1, 107-113; Korean Pat. Application No. 1996-44010). Also, as described in U.S. Pat. No. 6,027,888, a soluble eukaryotic protein having disulfide bonds can be produced by being expressed in a fused form with disulfide isomerase. In addition, as described in Korean Pat. Application No. 2002-0040497, an H-chain human ferritin protein can be produced as a soluble fusion protein with a L-chain human ferritin protein that is expressed in an insoluble form in *E. coli*. As described above, various attempts were made to express heterogeneous proteins in soluble fusion protein forms. However, the fusion effect varies according to the type of fusion proteins, as follows: fusion proteins are expressed as inclusion bodies; only a portion of them are expressed as soluble forms; and a protein fused with a target protein functions to aid the folding of the target protein (Savvas C. Makrides (1996), *Microbiological Review*, 512-538).

Thus, there is an urgent need for techniques allowing the high level production of biologically-active, soluble recombinant proteins in high efficiency and high concentrations.

DISCLOSURE OF THE INVENTION

Based on the above background, the present inventors intended to develop a novel vector system capable of producing in high levels a heterogeneous protein expressed as a biologically active form (but not inclusion bodies) in prokaryotes instead of finding fusion proteins useful for producing proteins by recombinant DNA technology.

As a result, the present inventors found that an expression vector system based on the polycistronic expression of a gene encoding a target protein and a beta-lactamase gene highly expresses both the target protein and beta-lactamase in prokaryotes, resulting in the expression of the target protein in a soluble form in a higher percentage, and is thus effective in the mass production of proteins. Using the established protein expression system, the present inventors developed a method of mass-producing a target protein in a biologically active form, thereby leading to the present invention.

It is therefore an object of the present invention to provide a method of producing a target protein expressed as a biologically active, soluble form instead of inclusion bodies, in prokaryotic cells.

It is another object of the present invention to provide a polycistronic vector system for producing the above target protein in a biologically active form.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
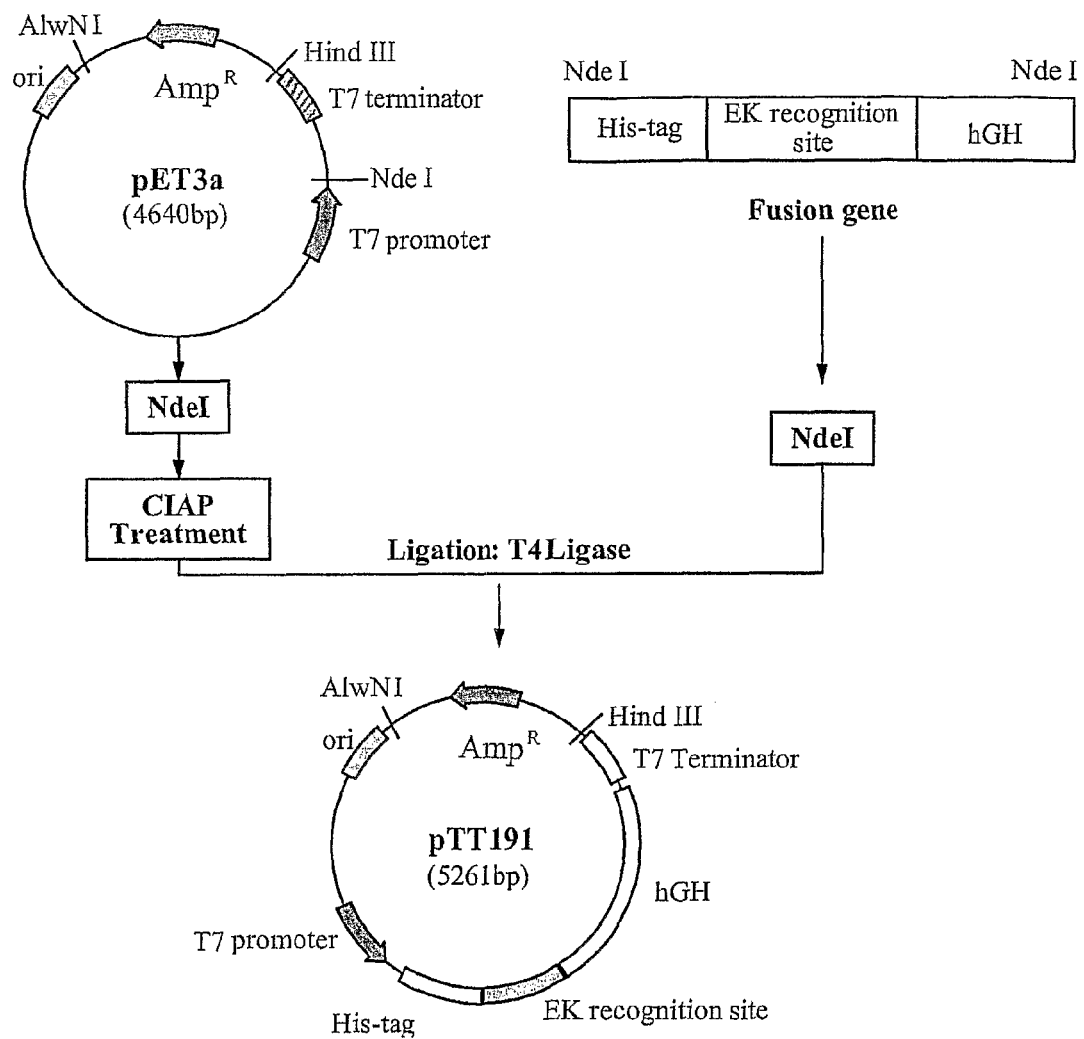
FIG. 1 is a diagram for a process of preparing an expression vector carrying a human growth hormone gene, pTT191.

In one aspect, the present invention relates to a method of producing an active, soluble target protein in a prokaryotic cell, which is based on expressing the target protein and beta-lactamase as a first cistron and a second cistron, respectively, in a citron.

The present inventors found that, when human growth hormone expressed as inclusion bodies in prokaryotic cells and beta-lactamase were polycistronically expressed, both human growth hormone and beta-lactamase were produced in high concentrations, and the expressed human growth hormone was present in an active, soluble form. In contrast, when basic fibroblast growth factor and keratinocyte growth factor were expressed using kanamycin instead of beta-lactamase under same conditions, the target proteins were mostly expressed as inclusion bodies. Based on this finding, the present inventors polycistronically coexpressed various target proteins that are expressed in the form of inclusion bodies in prokaryotic cells but have medical usefulness, with beta-lactamase. As a result, the target proteins in this system were produced in active, soluble forms.

Thus, in another aspect, the present invention relates to a polycistronic vector to produce a heterogeneous proteins in an active, soluble form.

In an embodiment, the present invention relates to a polycistronic vector for expressing target proteins in an active, soluble form in a prokaryotic cell, which comprises (i) a promoter operable in the prokaryotic cell, (ii) a first cistron including a DNA sequence encoding the target protein, and (iii) a second cistron including a DNA sequence encoding beta-lactamase.

The term "citron", as used herein, refers to a system where a single mRNA is synthesized from an same promoter, cistrons are separated from each other by a termination codon and an initiation codon, a ribosome binding site is present for each cistron, and proteins corresponding to each cistron are simultaneously expressed from the single mRNA transcribed in a single promoter. Herein, the "cistron" means a nucleotide sequence encoding for a single protein or polypeptide, and includes a 5' initiation codon and a 3' termination codon. In addition, the first and second cistrons do not mean the sequence in a DNA sequence but only indicate an individual cistron.

In a preferred aspect, in the citron of the present invention, the first cistron including a DNA sequence encoding a target protein may be in a 5' to 3' direction operably linked to the second cistron including a DNA sequence encoding beta-lactamase, or the second cistron including a DNA sequence encoding beta-lactamase may be in a 5' to 3' direction operably linked to the first cistron including a DNA sequence encoding a target protein.

The term "vector", as used herein, refers to a DNA construct that contains a DNA sequence operably linked to a suitable regulatory sequence capable of expressing DNA in a suitable host, and, in detail, may be constructed to contain a promoter sequence, a terminator sequence, a marker gene and other suitable sequences including a suitable regulatory sequence. Such a vector may be a plasmid, a pharge, a cosmid, or the like (Molecular Cloning: Laboratory Manual second edition, Sambrook et al., Cold Spring Harbor Laboratory Press (1989)). The preparation of such a vector, mutagenesis, sequence analysis, DNA introduction into cells, gene expression and protein analysis are described in detail in Current Protocols in Molecular Biology, edited by Ausubel et al., John Wiley & Sons (1992). When introduced into a suitable host, a vector may be replicated or function independently of the host genome, or, in some cases, may be integrated into the host genome. Plasmids are at present the most common form of vectors, and, in the present invention, the terms "plasmid" and "vector" may be used interchangeably. With respect to the objects of the present invention, a vector is a vector suitable for protein expression in prokaryotic cells, and is a polycistronic vector polycistronically expressing a heterogeneous target protein and beta-lactamase.

The term "operably linked", as used herein, means that an expression regulatory sequence is linked in such a way of regulating the transcription and translation of a polynucleotide sequence encoding a target protein, and includes maintaining a precise translation frame in such a way that a polypeptide of a target protein encoded by a polynucleotide sequence is produced when the polypeptide sequence is expressed under the control of regulatory sequences (including a promoter).

The term "promoter", as used herein, means a minimum sequence sufficient for triggering transcription. With respect to the objects of the present invention, a promoter inducible by an external signal or an effector is used. Promoters useful for the expression of a target protein in prokaryotic cells include T7, tac, trc, lac, lpp, phoA, recA, araBAD, prou, cst-1, tetA, cada, nar, lpp-lac, starvation promoters, cspA, T7-lac operator, T3-lac operator, T5-lac operator, T4 gene 32, and nprM-lac operator. Preferred are T7, tac, lac, T7-lac operator, T3-lac operator, T5-lac operator and T4 gene 32, and more preferred are T7, tac and T7-lac operator. The most preferred promoter is T7 promoter. T7 promoter can be controlled by T7 RNA polymerase and the expression of a T7 RNA polymerase can be controlled by IPTG(isopropyl-β-D-thiogalactosidase). T7 promoter can induce expression of a target protein in a desired time using IPTG. This is because it is preferable that a prokaryotic host cell, for example, *E. coli* is grown until a cell number is increased while a target protein is not expressed, and, after the *E. coli* cell number is sufficiently increased, the expression of the target protein is induced.

A ribosome binding site is typically located in about 10 bp upstream of an initiation codon, and functions to precisely and effectively initiate mRNA translation in polycistronic operon systems of phages or prokaryotes.

A target protein to be expressed using the polycistronic vector of the present invention may include all proteins having medical applications. In particular, proteins having demands for medical purposes but being known to be produced as inclusion bodies upon high expression in host cells by genetic engineering are suitable as the target protein of the present invention. Examples of the target protein include human growth hormone (hGH), granulocyte-colony stimulating factor (G-CSF), interferons (IFN), basic fibroblast growth factor (bFGF), insulin-like growth factor (IGF), keratinocyte growth factor (KGF), erythropoietin (EPO), thrombopoietin (TPO), human epidermal growth factor (EGF), platelet-derived growth factor (PDGF), vascular endothelial growth factor (VEGF), nerve growth factor (NGF), transforming growth factor (TGF), tumor necrosis factor (TNF), angiogenin, angiotensin, interleukin (IL), and tissue plasminogen activator (tPA). More preferred are hGH, G-CSF, IFN-α2b, bFGF, IGF-1, IGF-2, KGF, EPO, IL-7 and TPO. These target proteins may be in a natural or modified form, and may include their variants including deletions, substitutions or additions of the whole sequence or its fragment. In another embodiment of the present invention, hGH, G-CSF, IFN-α2b, bFGF, IGF-1, IGF-2 and KGF were expressed.

The target protein to be expressed in the present invention may be present itself, or may be present in the form of a fusion protein, such as a fused form with a sequence increasing solubility, to facilitate purification, provide various functions by being fused with an antibody or enzyme, or increase solubility. When the target protein contains a sequence facilitating, for example, purification, the target protein may be expressed in the form of a fusion protein with such a sequence. Such a fused target protein may be present in a sequence of a fusion partner-a peptide linker-a target protein, but may be prepared in various organizations according to the types of target proteins and fusion partners. More preferably, the fusion partner is employed for facilitating the purification of a produced protein, and is exemplified by histidine-tag, glutathione-S-transferase, maltose-binding protein, protein A, protein G, flag peptide, thioredoxin, S-peptide, avidin, streptavidin, galactose binding protein, cellulose-binding domain, chitin-binding domain, polyarginine, polycysteine and polyphenylalanine. In a further embodiment of the present invention, a histidine tag containing ten histidines was used. The peptide linker linking the target protein to such a fusion partner includes a sequence recognizable by a proteinase, and is exemplified by enterokinase, thrombin, factor Xa, urokinase, TEV protease and subtilisin, which have a high sequence specificity.

The term "active", as used herein, refers to a soluble protein that has biological activity by being stably expressed in a transformant with a recombinant vector and being folded into a native form without additional denaturation or refolding.

The term "soluble", as used herein, means the nature with which a protein is not easily precipitated in an aqueous solution and does not easily form inclusion bodies or other aggregates.

The beta-lactamase (bla) used in the present invention, as a factor for selecting a host cell transformed with an expression vector, is a protein providing a resistance to ampicillin. In the polycistronic vector of the present invention, the arrangement of a cistron encoding a target protein and another cistron encoding beta-lactamase may be changed by a certain purpose, but the cistron encoding beta-lactamase is preferably located in the downstream region of the cistron encoding a target protein.

pT0 expression vectors used in embodiments of the present invention are vectors in which a fused target protein gene (fusion partner-peptide linker-target protein gene) or a target protein gene itself is operably linked to the downstream region of T7 promoter of pET3a, and which overexpresses the target protein and beta-lactamase when the fused target protein gene (or the target protein gene) and a beta-lactamase gene are transcribed under the control of an same promoter. The pT0 expression vectors prepared in the present invention include pT0191, pT0-CSF pT0-IFN, pT0-bFGF, pT0-IGF1, pT0-IGF2, pT0-KGF and pT0N-KGF, which each carry fused hGH, G-CSF, IFN-α2b, bFGF, IGF-1, IGF-2 and KGF genes, and a non-fused KGF gene. When these vectors were expressed, most of the target proteins were expressed in soluble, active forms in comparison with a control.

On the other hand, the control expression vector of pTT used in embodiments of the present invention are vectors in which a fused target protein gene (fusion partner-peptide linker-target protein gene) is operably linked to the downstream region of T7 promoter of pET3a, but in which the fused target protein gene and a beta-lactamase gene are expressed under the control of different promoters. E. coli transformed with such a vector overexpressed the fused target protein in vivo, but a large quantity of the fusion protein was expressed as inclusion bodies (Example 2). Another control vector, pTR0191, is a plasmid prepared by converting a beta-lactamase gene to a reverse orientation in a pT0191 expression vector and operably linking a fused human growth hormone gene to the downstream region of T7 promoter, and in which the target protein and the beta-lactamase gene are not located under the control of the same promoter. When the pTR0191 was expressed in a host cell, the fusion protein was mostly expressed as inclusion bodies, and beta-lactamase was expressed in low levels (Example 5).

Thus, in one detailed aspect, to simultaneously overexpress beta-lactamase and a target protein itself or a target fusion protein and express the target protein in an active form in a higher percentage, the present invention provides polycistronic vectors, pT0191, pT0-CSF, pT0-IFN, pT0-bFGF, pT0-IGF1, pT0-IGF2, pT0-KGF and pT0N-KGF, which carry respectively genes encoding hGH (SEQ ID NO. 5), G-CSF (SEQ ID NO. 7), IFN-α2b (SEQ ID NO. 9), bFGF (SEQ ID NO. 11), IGF-1 (SEQ ID NO. 13), IGF-2 (SEQ ID NO. 15) and KGF (SEQ ID NO. 23), which are fused to a pT0 expression vector derived from a pET3a expression vector, and non-fused KGF (SEQ ID NO. 25). Of them, the pT0191 and pT0-IFN are introduced into E. coli BL21(DE3), and the pT0-CSF is introduced into E. coli BL21 Star(DE3)pLysS. The resulting transformants were deposited at KCTC (Korean Collection for Type Cultures; KRIBB, 52, Oun-dong, Yusong-ku, Taejon, Korea) on Mar. 11, 2004, under accession numbers KCTC-10610BP, KCTC-10612BP and KCTC-10611BP, respectively.

The polycistronic expression vectors of the present invention may be introduced into a host cell to transform the host cell by certain methods known in the art, including chemical methods using $CaCl_2$ and electroporation.

The term "transformed", as used herein, refers to introduction into a prokaryotic cell in such a manner as to allow a gene carried by the polycistronic vector to be expressed.

If a recombinant nucleotide sequence of a fusion protein is suitably transcribed to mRNA in a cell, and the cell is able to express proteins, a certain prokaryotic cell can be used, and a Gram-negative bacterium, E. coli, and a Gram-positive bacterium, Bacillus, are preferred. More preferred is E. coli, and most preferred are E. coli BL21 (DE3), E. coli BL21 Star (DE3)pLysS, E. coli HMS (DE3) and E. coli AD494 (DE3). The above host cells possess bacteriophage $T_7$ RNA polymerase, and the present invention is not limited to the examples. The bacteriophage-derived T7 promoter used in the present invention is more effectively expressed by bacteriophage $T_7$ RNA polymerase than by E. coli RNA polymerase (Studier F W et al. (1990), *Method Enzymol.* 185, 60-89). Thus, the pT0 expression vectors are preferably expressed by being introduced into E. coli BL21 (DE3) or E. coli BL21 Star (DE3) pLysS which carries $T_7$ RNA polymerase gene under control of the lacUV5 promoter. When the pT0-CSF expression vector of the present invention is introduced into E. coli BL21 (DE3), BL21 Star (DE3) pLysS, HMS (DE3) or AD494(DE3), a target fusion protein may be expressed in an active form with an efficiency of 70% or higher.

Thus, in still another aspect, the present invention provides transformants transformed with the above polycistronic expression vectors. In detail, the transformants include E. coli transformed with pT0191, pT0-CSF, pT0-IFN, pT0-bFGF, pT0-IGF1, pT0-IGF2, pT0-KGF or pT0N-KGF.

The transformants transformed with the expression vectors according to the present invention are cultured in suitable media under suitable conditions in a manner of allowing a DNA sequence encoding a target protein to be expressed. A method of expressing a recombinant protein by culturing a transformant is known in the art. For example, a transformant is inoculated in a suitable medium for seed culture, and the seed culture is inoculated in a production culture medium and grown under suitable conditions, thereby inducing protein expression. In the production culture, microbial growth is performed separately from the induction of recombinant protein expression, thereby increasing recombinant protein yield.

Thus, in still another aspect, the present invention provides a method of producing an active, soluble protein, comprising culturing the transformant and recovering a soluble target protein from a culture.

From the culture obtained by culturing a transformant, a target protein is recovered in substantially pure forms, and thus can be used for medical purposes. The recovery of a recombinant protein may be achieved by various isolation and purification methods known in the art. Typically, to remove cell debris, a cell lysate is centrifuged, and the supernatant is subjected to precipitation, dialysis and various column chromatographies. Examples of the column chromatography include ion exchange chromatography, gel-filtration chromatography, HPLC, reverse phased HPLC, preparative SDS-PAGE, and affinity column chromatography.

The purification of the soluble, active protein according to the present invention may be achieved by typical purification methods such as ultrafiltration and ion exchange chromatography without a refolding process after cell disruption and centrifugation, thereby facilitating the isolation of an active target protein.

A better understanding of the present invention may be obtained through the following examples which are set forth to illustrate, but are not to be construed as the limit of the present invention.

EXAMPLE 1

Construction of pTT191 Expression Vector

A control expression vector pTT191 was prepared to express in high yields a fusion protein containing human growth hormone as inclusion bodies.

A fusion gene encoding a fusion protein (SEQ ID NO. 5) containing human growth hormone, which is linked to a histidine-tag and an enterokinase recognition sequence, was prepared by a PCR ligation method (PCR ligation method, Willem P. C. Stemmer, and Herbert L. Heyneker (1995) Gene 164, 49-53; Scott W. Altmann, and Robert A. Kastelein (1995) Protein Expression and Purification 6, 722-726; Ana Paula de Mattos Areas, and Paulo Lee Ho (2002) Protein Expression and Purification 25, 481-487). The PCR ligation method was carried out as follows. To a PCR tube, 50 pmole of each of pairs of synthetic oligonucleotides containing twenty complementarily overlapped bases, 2.5 U (1 μl) of Pfu DNA polymerase (Stratagene, USA), 2 μL of 2.5 mM dNTPs (Takara, Japan), and 2 μl of 10×Pfu polymerase buffer were sequentially added, and sterile distilled water was added to a final volume of 20 μl. PCR was carried out using a PCR machine (MJ research, USA). Herein, each of the oligonucleotides served as a template as well as a primer. PCR conditions included denaturation at 94° C. for 5 min, and 20 cycles of denaturation at 95° C. for 1 min, annealing at 52° C. for 30 sec and elongation at 72° C. for 30 sec, followed by final elongation at 72° C. for 10 min. Two PCR products having a complementary nucleotide sequence (20 bp) at ends were amplified. To a PCR tube, 5 μl of each of the PCR products, 2.5 U (1 μl) of Pfu DNA polymerase (Stratagene, USA), 2 μl of 2.5 mM dNTPs (Takara, Japan), and 2 μl of 10×Pfu polymerase buffer were sequentially added, and sterile distilled water was added to a final volume of 20 μl. PCR was carried out using a PCR machine (MJ research, USA). PCR conditions included denaturation at 94° C. for 5 min, and 20 cycles of denaturation at 95° C. for 1 min, annealing at 52° C. for 30 sec and elongation at 72° C. for 30 sec, followed by final elongation at 72° C. for 10 min. This procedure was repeated, and, in a final step, PCR was carried with 30 cycles, thus generating a synthetic gene. The synthesized gene was run on a 1% agarose gel and isolated from the gel using QIAQuick gel extraction kit (Qiagen, USA). As a result, a fused human growth hormone (somatotropin) gene (SEQ ID NO. 5) was obtained, which included a histidine-tag (SEQ ID NO. 1) and an enterokinase recognition sequence (SEQ ID NO. 3) and an Nde I recognition sequence at both ends. Thereafter, the pTT191 expression vector was constructed as shown in FIG. 1. The synthesized fusion gene was digested with NdeI, separated on a 1% agarose gel, and isolated from the gel. The linearized fusion gene was ligated to NdeI-digested pET3a (Novagen, USA) that was also pretreated with CIAP (calf intestine alkaline phosphatase; NEB, USA). The CIAP treatment was carried out at 37° C. for one hour to prevent self-ligation of the NdeI-digested pET3a. The ligation was carried out at 16° C. for 18 hrs using T4 DNA ligase (NEB, USA), thus generating pTT191. Then, E. coli TOP10 (Invitrogen, USA) was transformed with the pTT191. The plasmid DNA was prepared from the resulting transformant and introduced into E. coli BL21 (DE3) (Novagen, USA). The resulting E. coli BL21 (DE3) transformant transformed with the pTT191 expression vector was selected on ampicillin-containing LB plates, and designated as "E. coli BL21 (DE3)/pTT191". The correct insertion of the fusion gene containing a human growth hormone gene in the pTT191 expression vector was confirmed by digestion with restriction enzymes AlwNI and HindIII and DNA sequencing.

EXAMPLE 2

Expression of the Fusion Protein with Human Growth Hormone in the E. Coli BL21 (DE3)/pTT191 Transformant The expression pattern of the fusion protein with human growth hormone was tested in E. coli transformed with the control expression vector pTT191.

Figure 2:
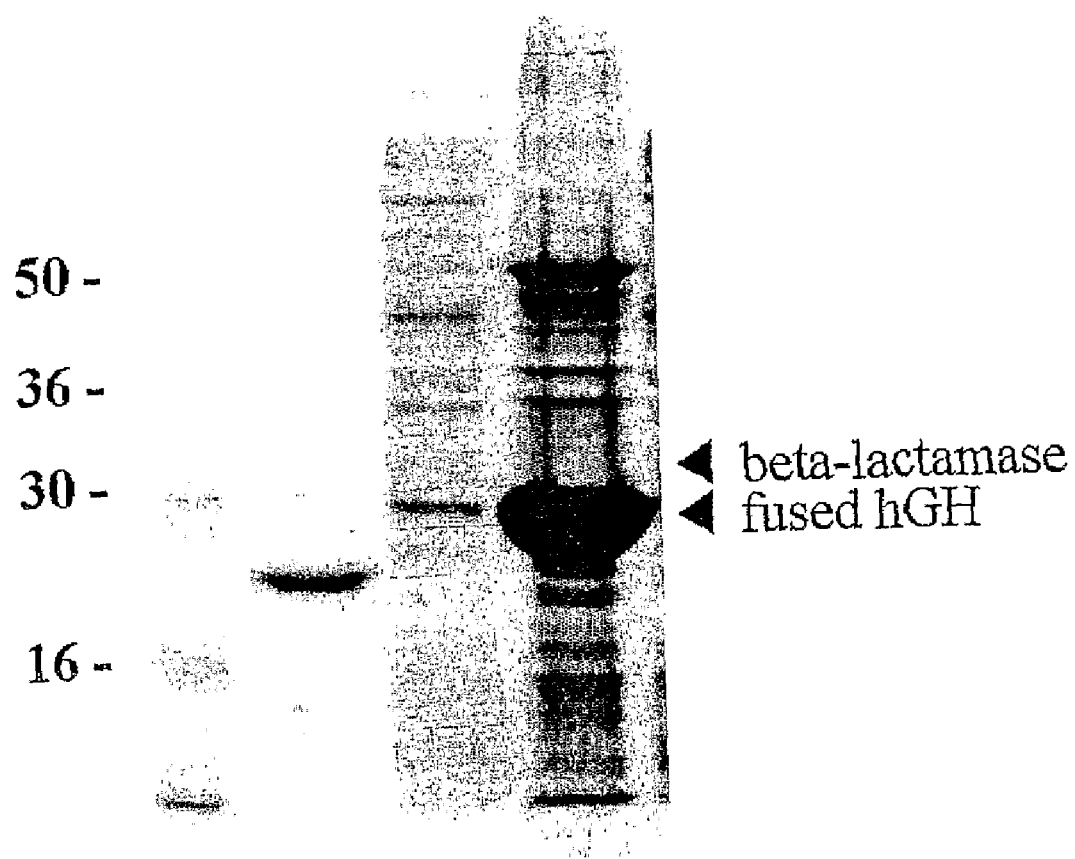
FIG. 2 is a photograph showing a result of analysis for human growth hormone expression on a SDS-PAGE gel after *E. coli* BL21 (DE3) was transformed with a pTT191 expression vector (lane 1: protein size marker; lane 2: standard of human growth hormone; lane 3: supernatant obtained by disrupting the IPTG-induced transformant; and lane 4: pellet obtained by disrupting the IPTG-induced transformant)

The E. coli BL21 (DE3)/pTT191 transformed with the pTT191 expression vector was cultured in LB medium (Luria-Bertani medium) at 30° C. for 12 hrs, and the expression of the fusion protein was then induced with IPTG (Isopropyl-β-D-Thiogalactopyranoside). After IPTG induction, cells were collected by centrifugation and disrupted. After centrifugation, the supernatant was used to investigate the expression of the fusion protein. As a result, as shown in FIG. 2, the fusion protein containing human growth hormone had the predicted molecular weight of about 24 kDa, but mainly expressed as inclusion bodies.

EXAMPLE 3

Construction of pT0191 Expression Vector

A pT0191 expression vector was prepared to express the fusion protein containing human growth hormone in a soluble form in a higher percentage.

Figure 3:
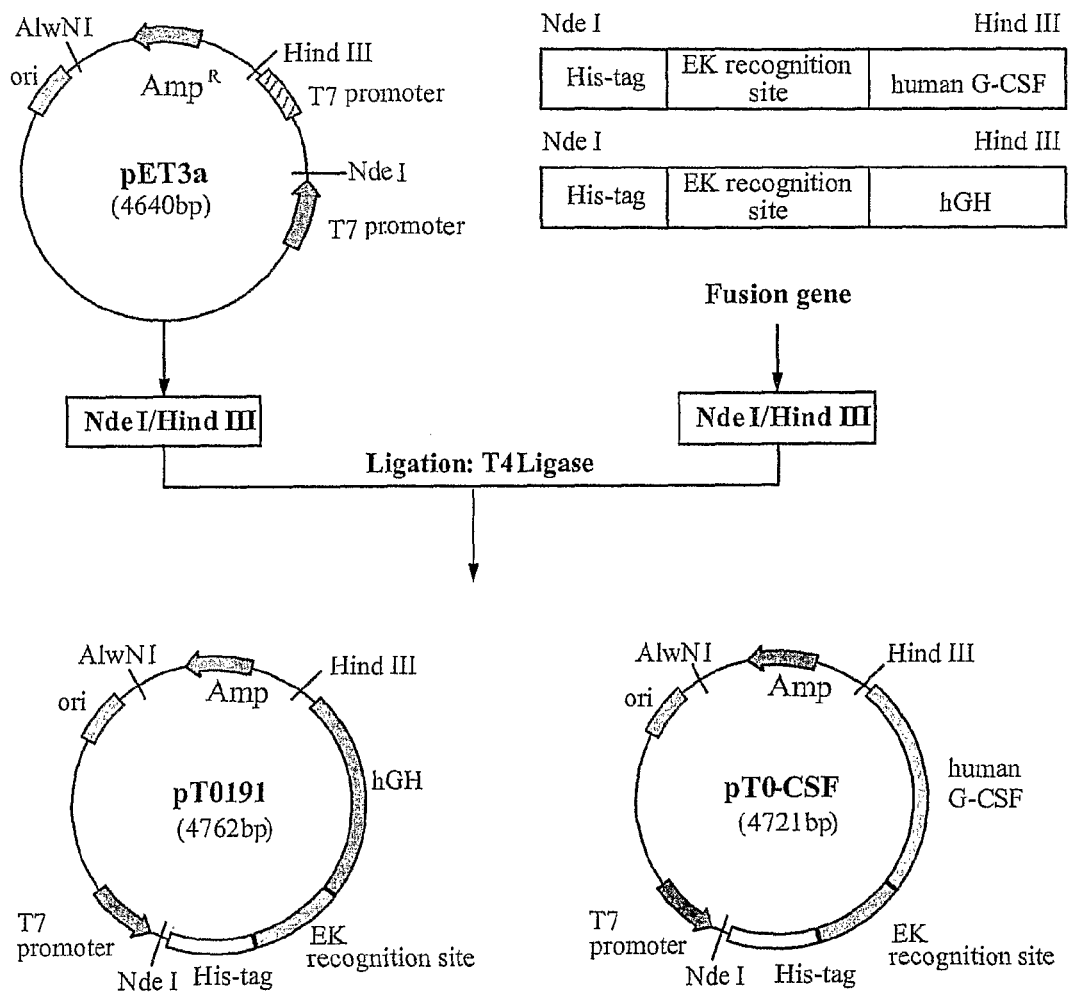
FIG. 3 is a diagram for a process of preparing pT0191 and pT0-CSF expression vectors respectively carrying a human growth hormone (hGH) gene and a human granulocyte-colony stimulating factor (G-CSF) gene.

To insert a gene encoding the fusion protein with human growth hormone into a pET3a vector, PCR was carried out using pTT191 as a template, thus providing an NdeI recognition site and a HindIII recognition site to each end of a nucleotide sequence encoding the fusion protein. To a PCR tube, 100 ng of pTT191 plasmid (Example 1) as a template, 2.5 U (1 µl) of Pfu DNA polymerase (Stratagene, USA), 30 pmole of primer A (5'-AAACATATGGGCCATCATCAT-CATCATCATCATCATCATCAC-3': SEQ ID NO. 19), 30 pmole of primer B (5'-AAAAAGCTTTTACTAGAAGCCA-CAGCTGCC-3': SEQ ID NO. 20), 2 µl of 2.5 mM dNTPs (Takara, Japan), and 2 µl of 10×Pfu polymerase buffer were sequentially added, and sterile distilled water was added to a final volume of 20 µl. PCR was carried out using a PCR machine (MJ research, USA). PCR conditions included denaturation at 94° C. for 5 min, and 30 cycles of denaturation at 95° C. for 1 min, annealing at 58° C. for 30 sec and elongation at 72° C. for 2 min, followed by final elongation at 72° C. for 10 min. The amplified gene was digested with NdeI and HindIII restriction enzymes, separated on a 1% agarose gel and purified from the gel. The pET3a expression vector was digested with NdeI and HindIII and separated on a 1% agarose gel, and a 4119-bp fragment was purified from the gel. The NdeI/HindIII-treated fusion gene and pET3a fragment were ligated to each other at 16° C. for 18 hrs using T4 DNA ligase, thus generating pT0191. Then, *E. coli* TOP10 (Invitrogen, USA) was transformed with the pT0191 (FIG. 3). The plasmid DNA was prepared from the resulting transformant and introduced into *E. coli* BL21 (DE3). The resulting *E. coli* BL21 (DE3) transformant transformed with the pT0191 expression vector was selected on ampicillin-containing LB plates, and designated as "*E. coli* BL21 (DE3)/pT0191 (KCTC10610BP)". The correct insertion of the fusion gene containing a human growth hormone gene in the pT0191 expression vector was confirmed by digestion with restriction enzymes NdeI and HindIII and DNA sequencing.

EXAMPLE 4

Expression of the Fusion Protein with Human Growth Hormone in the *E. Coli* BL21(DE3)/pT0191 Transformant The expression pattern of the fusion protein with human growth hormone was tested in *E. coli* transformed with the pT0191 expression vector.

Figure 4:
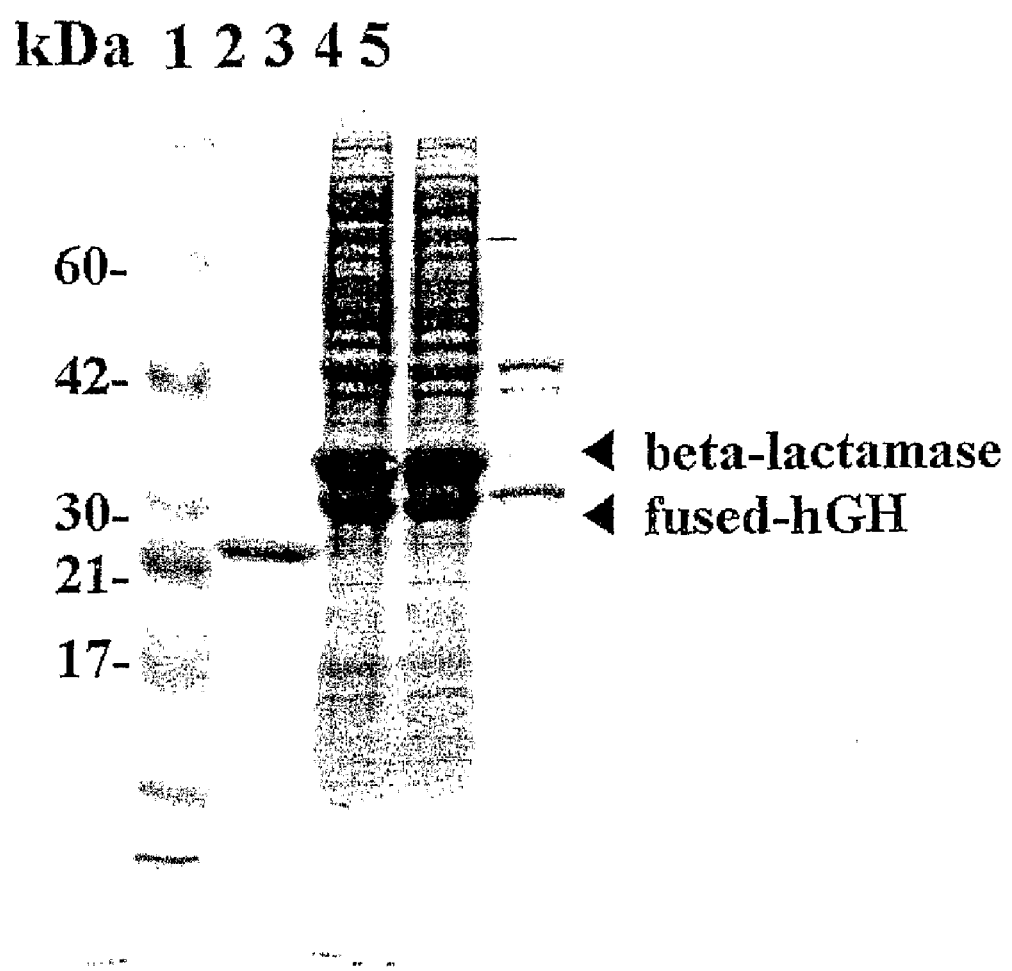
FIG. 4 is a photograph showing a result of analysis for human growth hormone expression on a SDS-PAGE gel after *E. coli* BL21 (DE3) was transformed with a pT0191 expression vector (lane 1: protein size marker; lane 2: standard of human growth hormone; lane 3: whole proteins obtained by disrupting the IPTG-induced transformant; lane 4: supernatant obtained by disrupting the IPTG-induced transformant; and lane 5: pellet obtained by disrupting the IPTG-induced transformant)

The *E. coli* BL21 (DE3)/pT0191 transformed with the pT0191 expression vector was cultured in LB medium at 30° C. for 12 hrs, and the expression of the fusion protein was then induced with IPTG. Thereafter, the expression of the fusion protein was estimated. As shown in FIG. 4, the fusion protein mainly expressed in an active form and was present in a centrifuged supernatant, and had a molecular weight of about 24 kDa. Unlike the *E. coli* BL21 (DE3)/pTT191 transformant, the *E. coli* BL21 (DE3)/pT0191 transformant was found to overexpress the target fusion protein along with beta-lactamase. The expression of beta-lactamase was confirmed by N-terminal sequencing.

EXAMPLE 5

Construction of pTR0191 Expression Vector and Expression of Human Growth Hormone in *E. Coli* BL21 (DE3)/pTR0191 Transformant The pT0191 plasmid prepared in Example 3 was digested with SphI and HindIII, and a 3812-bp fragment was purified.

Figure 5:
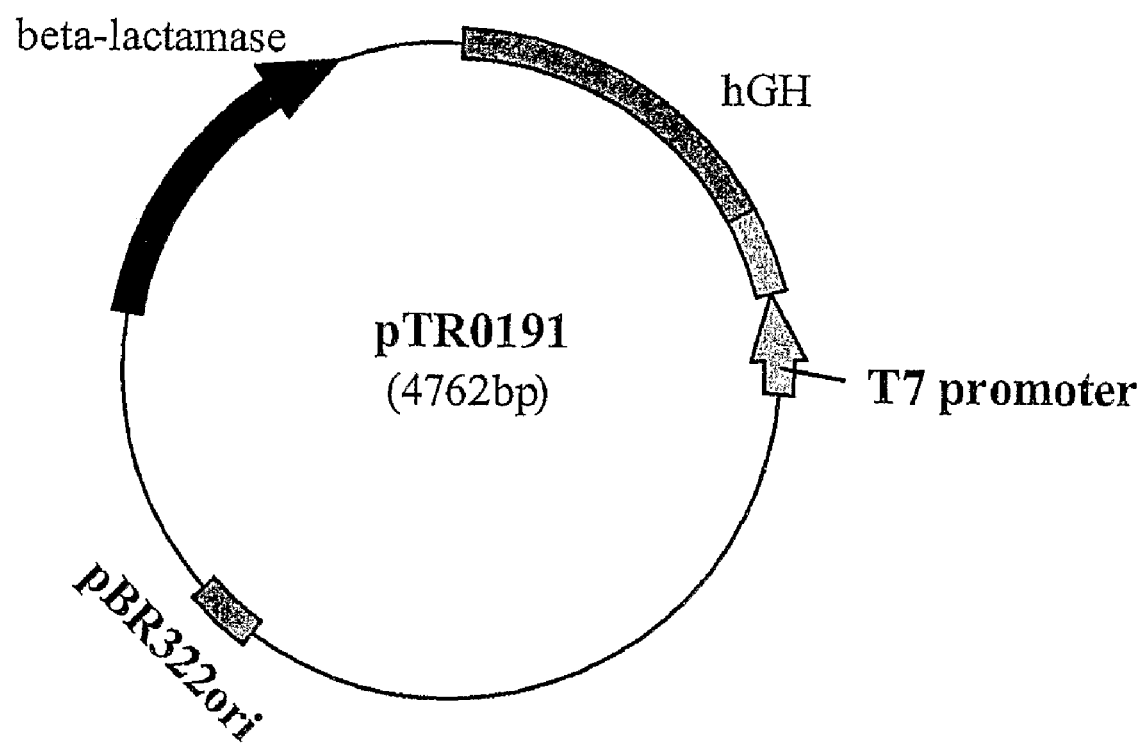
FIG. 5 is a construct of a pTR0191 prepared by inserting a human growth hormone (hGH) gene into an expression vector carrying a beta-lactamase gene in a reverse-orientation to the hGH gene.
Figure 6:
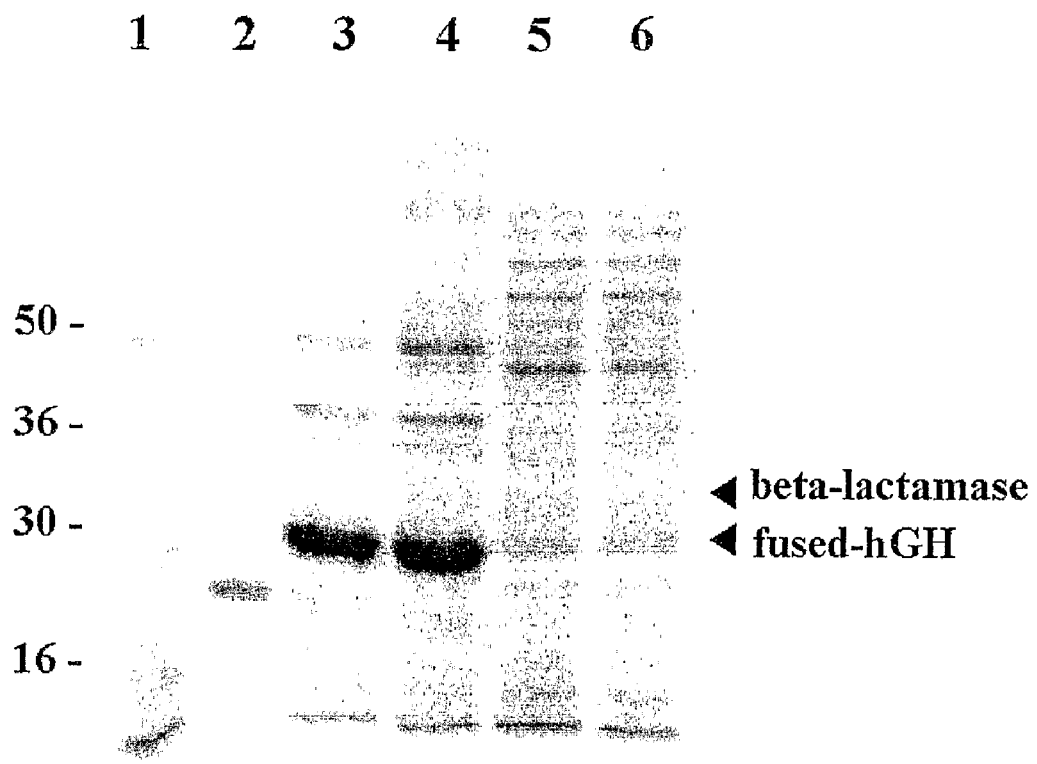
FIG. 6 is a photograph showing a result of analysis for human growth hormone expression on a SDS-PAGE gel after *E. coli* BL21 (DE3) was transformed with a pTR0191 expression vector (lane 1: protein size marker; lane 2: standard of human growth hormone; lanes 3 and 4: pellets obtained by disrupting the IPTG-induced transformant; and lane 5 and 6: supernatants obtained by disrupting the IPTG-induced transformant)

A gene encoding beta-lactamase contained in the pT0191 plasmid was amplified by PCR using two primers (primer 1: 5'-AAAAAGCTTAAGGAGATGGCGCCCA-3' (SEQ ID NO. 21); primer 2: 5'-AAAGCATGCCTAGAAGCCA-CAGCTG-3' (SEQ ID NO. 22)), thus generating a 950-bp fragment in which the positions of the SphI and HindIII sites were exchanged with each other. Then, the 950-bp fragment was ligated to the 3812-bp fragment using T4 DNA ligase, thus generating a pTR0191 expression vector in which the human growth hormone gene had a different orientation from the beta-lactamase gene (FIG. 5). *E. coli* BL21 (DE3) was transformed with the prepared expression vector, and protein expression was carried out at 30° C. As shown in FIG. 6, the target protein was expressed mainly as inclusion bodies, and the beta-lactamase was expressed in lower levels than the case of using the pT0191 expression vector.

EXAMPLE 6

Construction of pT0-CSF Expression Vector

A pT0-CSF expression vector was prepared to express in high yields a fusion protein containing human granulocyte-colony stimulating factor (G-CSF) in a soluble form. A gene (SEQ ID NO. 7) encoding a fusion protein containing human G-CSF linked to a histidine-tag and an enterokinase recognition sequence was synthesized according to the same PCR ligation method as in Example 1, and the pT0-CSF expression vector was constructed according to the same method as in Example 3 (FIG. 3). The pT0-CSF expression vector was introduced into *E. coli* BL21 Star(DE3) pLysS (Invitrogen, USA), and the resulting transformant was designated as "*E. coli* BL21 Star(DE3)pLysS/pT0-CSF (KCTC10611BP)". The correct insertion of the fusion gene containing a human G-CSF gene into the pT0-CSF expression vector was confirmed by digestion with NdeI and HindIII and DNA sequencing.

EXAMPLE 7

Expression of the Fusion Protein with Human G-CSF in the *E. coli* B21 Star(DE3)pLysS/pT0-CSF Transformant The expression pattern of the fusion protein with human G-CSF was investigated in *E. coli* transformed with the pT0-CSF expression vector.

Figure 7:
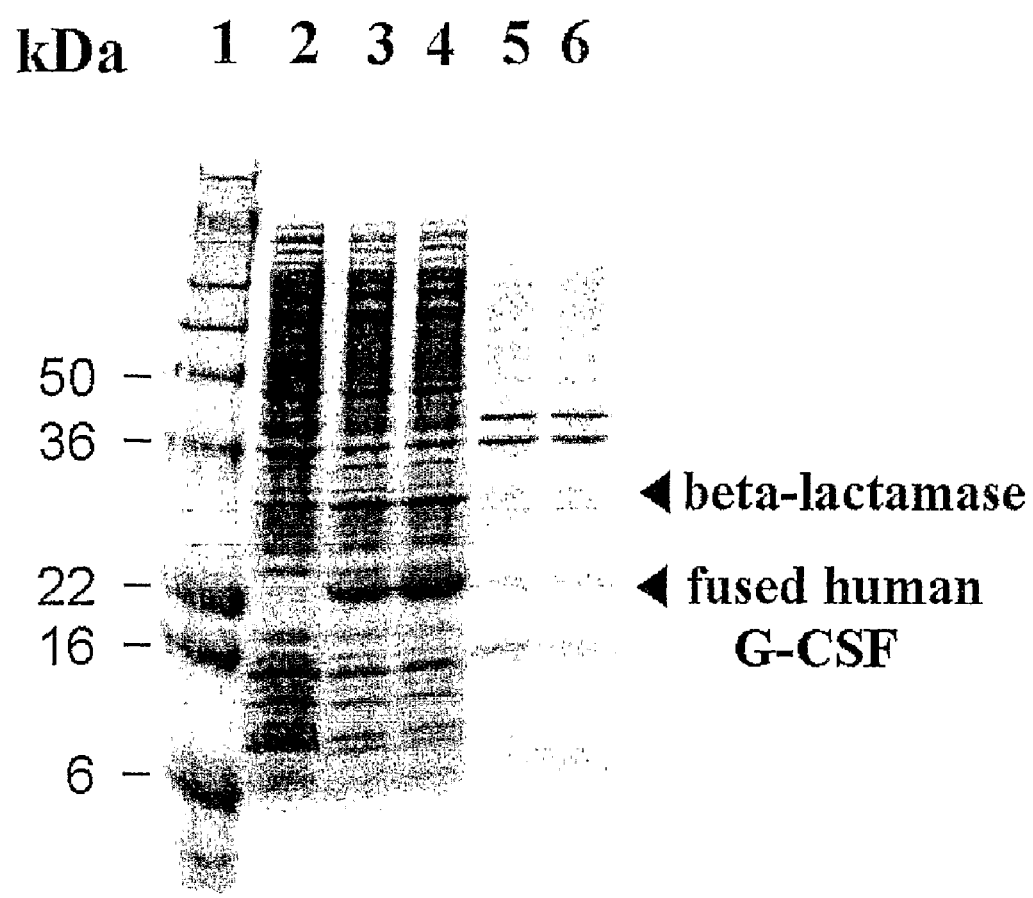
FIG. 7 is a photograph showing a result of analysis for human G-CSF expression on a SDS-PAGE gel after *E. coli* BL21Star(DE3)pLysS was transformed with a pT0-CSF expression vector (lane 1: protein size marker; lane 2: supernatant obtained by disrupting the transformant before IPTG induction; lanes 3 and 4: supernatants obtained by disrupting the IPTG-induced transformant; and lane 5 and 6: pellets obtained by disrupting the IPTG-induced transformant)
Figure 8:
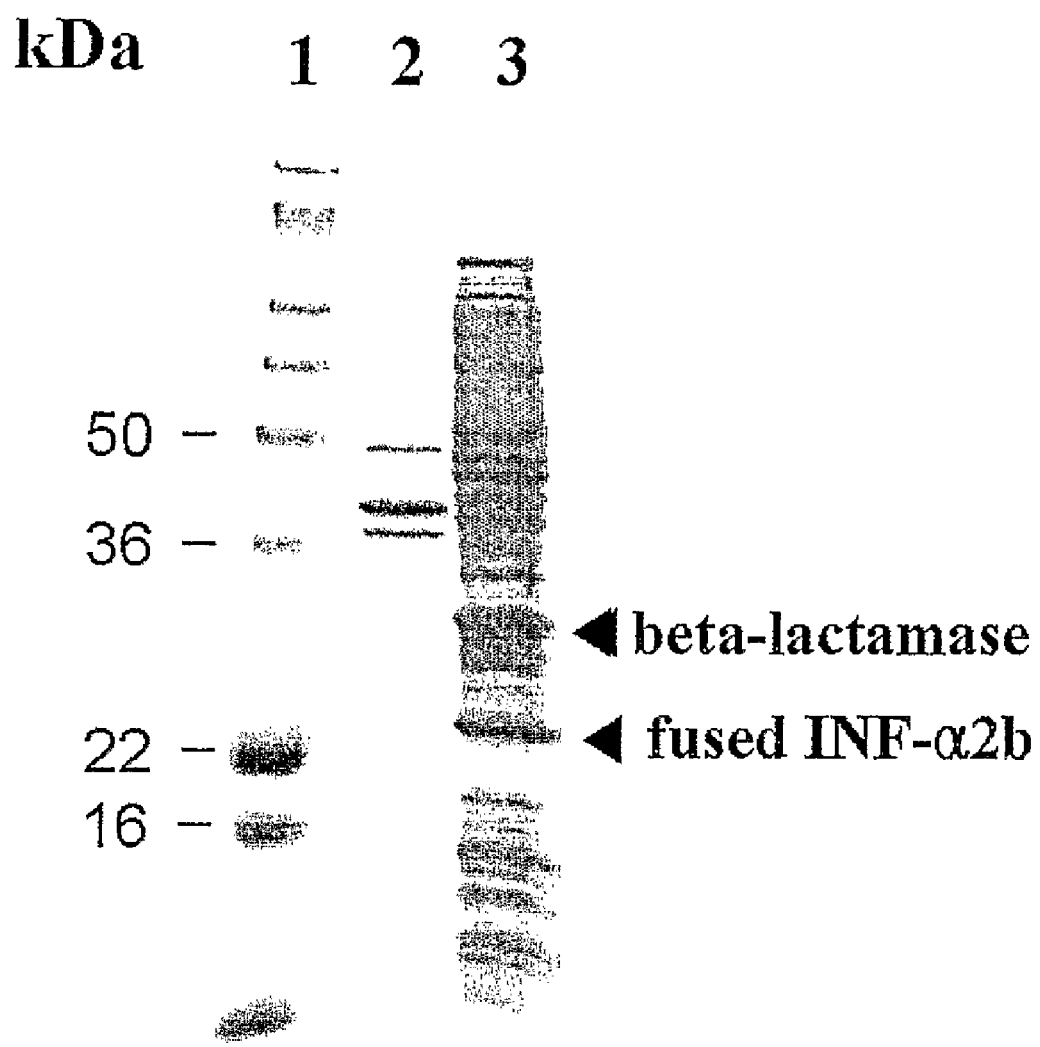
FIG. 8 is a photograph showing a result of analysis for interferon-α2b expression on a SDS-PAGE gel after *E. coli* BL21(DE3) was transformed with a pT0-IFN expression vector (lane 1: protein size marker; lane 2: pellet obtained by disrupting the IPTG-induced transformant; and lane 3: supernatants obtained by disrupting the IPTG-induced transformant)
Figure 9:
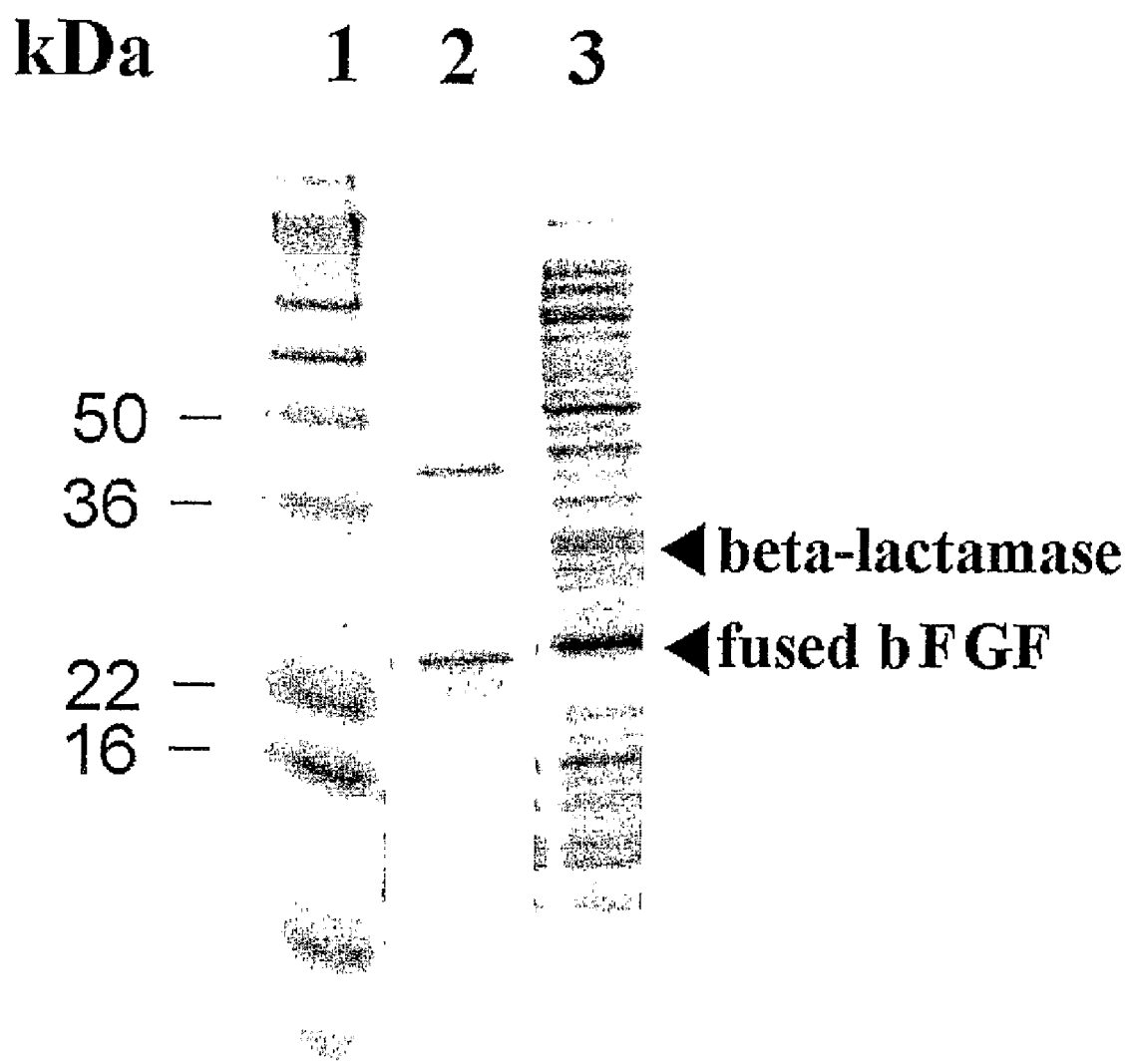
FIG. 9 is a photograph showing a result of analysis for basic fibroblast growth factor expression on a SDS-PAGE gel after *E. coli* BL21(DE3) was transformed with a pT0-bFGF expression vector (lane 1: protein size marker; lane 2: pellets obtained by disrupting the IPTG-induced transformant; and lane 3: supernatants obtained by disrupting the IPTG-induced transformant)
Figure 10:
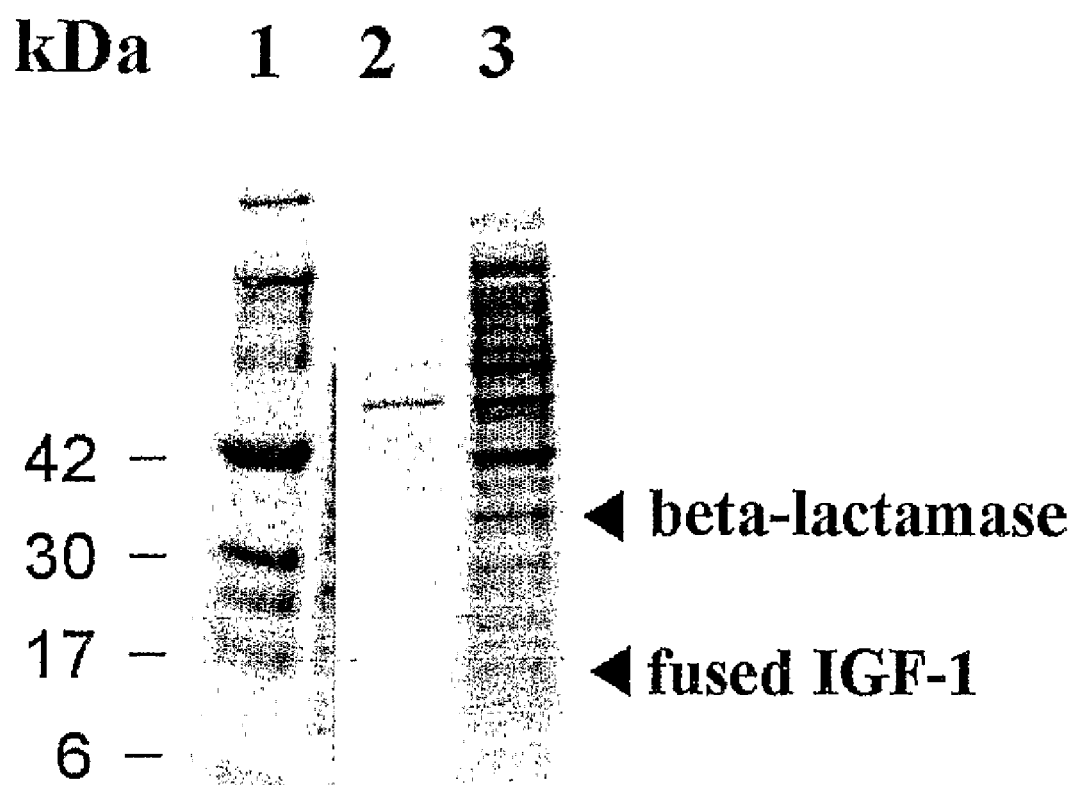
FIG. 10 is a photograph showing a result of analysis for insulin-like growth factor-1 expression on a SDS-PAGE gel after *E. coli* BL21(DE3) was transformed with a pT0-IGF1 expression vector (lane 1: protein size marker; lane 2: pellet obtained by disrupting the IPTG-induced transformant; and lane 3: supernatant obtained by disrupting the IPTG-induced transformant)
Figure 11:
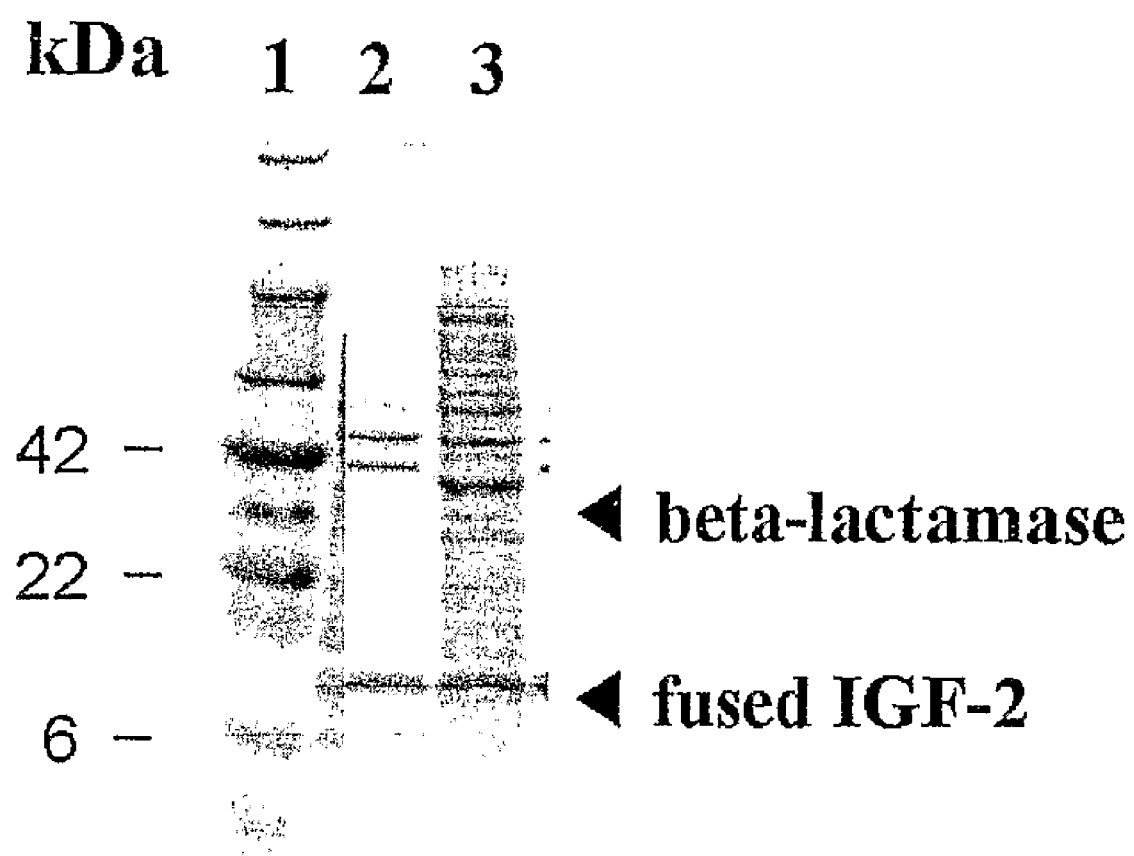
FIG. 11 is a photograph showing a result of analysis for insulin-like growth factor-2 expression on a SDS-PAGE gel after *E. coli* BL21(DE3) was transformed with a pT0-IGF2 expression vector (lane 1: protein size marker; lane 2: pellet obtained by disrupting the IPTG-induced transformant; and lane 3: supernatant obtained by disrupting the IPTG-induced transformant)
Figure 12:
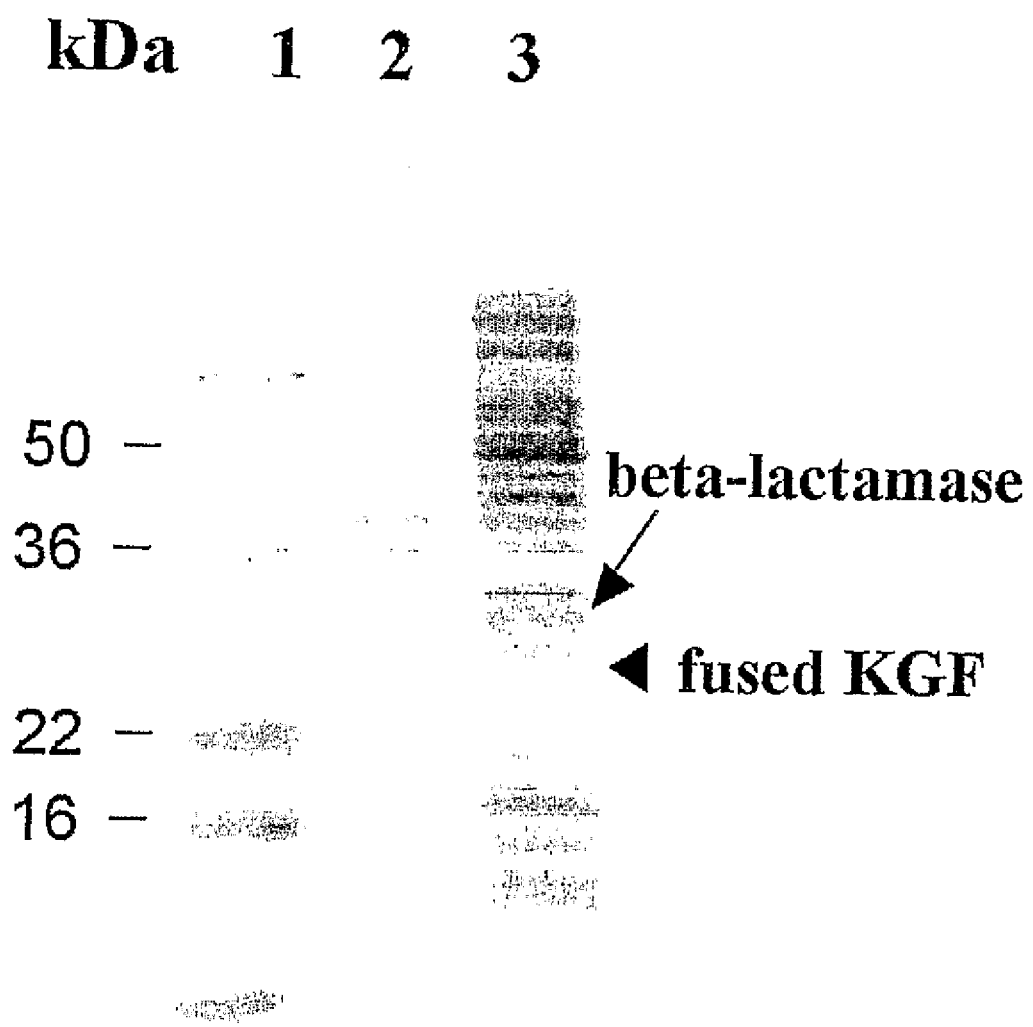
FIG. 12 is a photograph showing a result of analysis for keratinocyte growth factor expression on a SDS-PAGE gel after *E. coli* BL21(DE3) was transformed with a pT0-KGF expression vector (lane 1: protein size marker; lane 2: pellets obtained by disrupting the IPTG-induced transformant; and lane 3: supernatant obtained by disrupting the IPTG-induced transformant)
Figure 13:
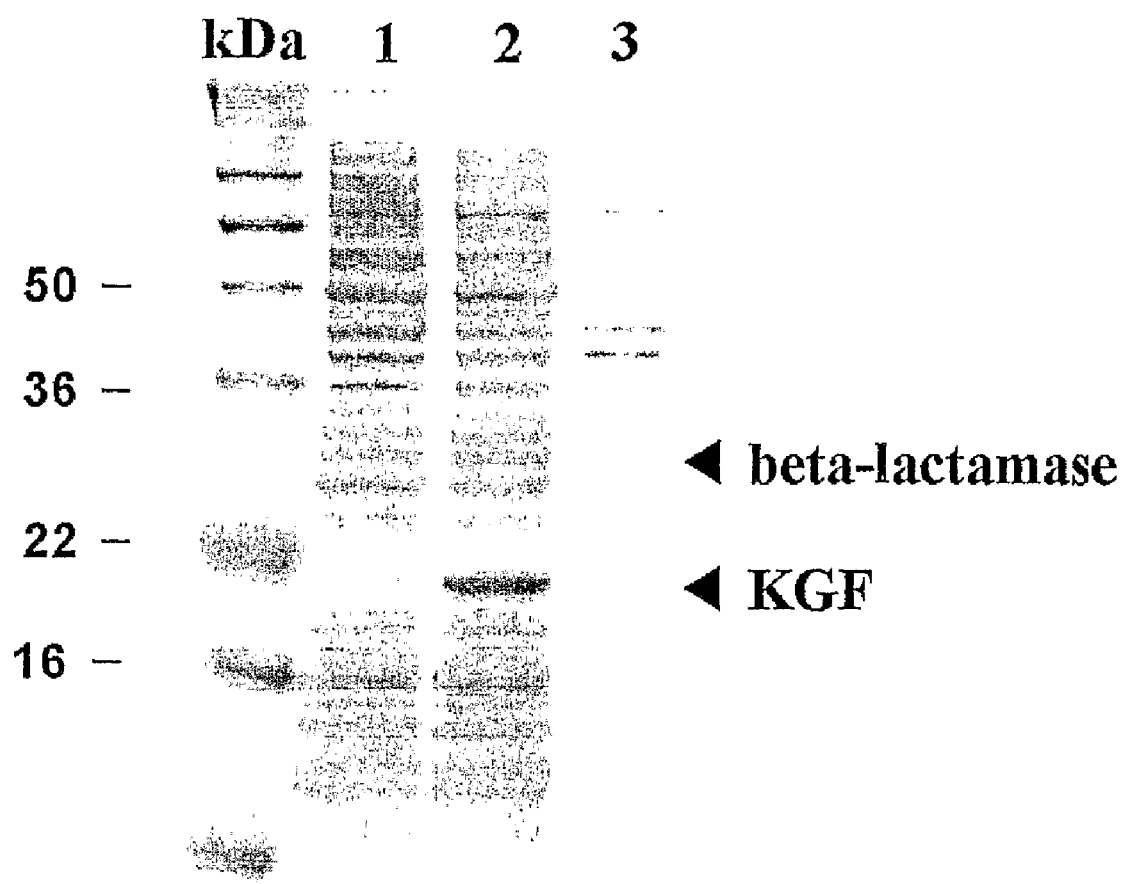
FIG. 13 is a photograph showing a result of analysis for keratinocyte growth factor expression on a SDS-PAGE gel after *E. coli* BL21(DE3) was transformed with a pT0N-KGF expression vector (lane 1: protein size marker; lane 2: pellets obtained by disrupting the IPTG-induced transformant; and lane 3: supernatants obtained by disrupting the IPTG-induced transformant).

The *E. coli* B21 Star(DE3)pLysS/pT0-CSF transformed with the pT0-CSF expression vector was cultured in LB medium at 30° C. for 12 hrs, and the expression of the fusion protein was then induced with IPTG. As shown in FIG. 7, the fusion protein containing human G-CSF was expressed mainly in an active form and present in a centrifugal supernatant, and had a molecular weight of about 20 kDa. Like the *E. coli* BL21 (DE3)/pT0191 transformant, the *E. coli* B21 Star(DE3)pLysS/pT0-CSF transformant transformed with the pT0-CSF expression vector was found to overexpress the target fusion protein containing human G-CSF along with beta-lactamase.

In addition, the pT0-CSF expression vector was introduced into *E. coli* BL21 (DE3) (Novagen, USA), *E. coli* HMS (DE3) (Novagen, USA) and *E. coli* AD494 (DE3) (Novagen, USA) to investigate the expression pattern of the fusion protein containing human G-CSF (also designated herein as human G-CSF fusion protein) in the *E. coli* strains. The results are given in Table 1, below. As apparent from the data of Table 1, the fusion protein was mainly expressed in an active form.

TABLE 1

| Host cell (E.coli) | Volume (arbitary unit [a.u.]) | | | |
|---|---|---|---|---|
| | Total | Active form | Inclusion bodies | Percentage of active form* |
| BL21 (DE3) | 15,043 | 10,610 | 4,433 | 70.5% |
| BL21 Star (DE3) pLysS | 28,169 | 25,554 | 2,614 | 90.7% |
| HMS (DE3) | 13,376 | 12,361 | 1,015 | 92.4% |
| AD 494 (DE3) | 22,843 | 16,886 | 5,957 | 73.9% |

*measured by a densitometer after electorphoresis

EXAMPLE 8

Construction of pT0-IFN, pT0-bFGF, pT0-IGF1, pT0-IGF2, pT0-KGF and pT0N-KGF Expression Vectors Several expression vectors, pT0-IFN, pT0-bFGF, pT0-IGF1, pT0-IGF2, pT0-KGF and pT0N-KGF, were prepared to express in high yields various target proteins themselves or fusion proteins containing target proteins in soluble forms. Genes coding for an IFN-α2b fusion protein (SEQ ID NO. 9), a bFGF fusion protein (SEQ ID NO. 11), an IGF-1 fusion protein (SEQ ID NO. 13), an IGF-2 fusion protein (SEQ ID NO. 15) and a KGF fusion protein (SEQ ID NO. 23), which each are linked to a histidine-tag and an enterokinase recognition sequence, and a non-fused KGF itself (SEQ ID NO. 25) were prepared according to the same PCR ligation method as in Example 1, wherein primers were designed to provide a NdeI site and a HindIII site at each end of a sequence of each of the coding genes to insert fusion protein into pET3a vector. The amplified genes were digested with NdeI and HindIII, separated on a 1% agarose gel, and purified from the gel. A pET3a expression vector was digested with NdeI and HindIII and separated on a 1% agarose gel, and a 4119-bp fragment was purified from the gel. Each of the NdeI/HindIII-treated fused genes and pET3a fragment was ligated to each other at 16° C. for 18 hrs using T4 DNA ligase, thus generating expression vectors, pT0-IFN, pT0-bFGF, pT0-IGF1, pT0-IGF2, pT0-KGF and pT0N-KGF, respectively. Then, E. coli TOP10 was transformed with the expression vectors. The plasmid DNA was prepared from each of the resulting transformants and introduced into E. coli BL21 (DE3). The correct insertion of each gene into the corresponding expression vector was confirmed by digestion with NdeI and HindIII and DNA sequencing.

EXAMPLE 9

Expression of Each Target Protein in E. Coli BL21 (DE3)/pT0-IFN, pT0-bFGF, pT0-IGF1, pT0-IGF2, pT0-KGF and pT0N-KGF Transformants The expression pattern of each target protein was investigated in E. coli transformed with the expression vectors, pT0-IFN, pT0-bFGF, pT0-IGF1, pT0-IGF2, pT0-KGF and pT0N-KGF.

The E. coli BL21 (DE3) transformants transformed with the above expression vectors were individually cultured in LB medium at 30° C. for 12 hrs, and the expression of each target protein was then induced with IPTG. The results are given in FIGS. 8 to 13. As shown in the figures, the expressed target proteins were present in a centrifugal supernatant, thus indicating that the target proteins are expressed in soluble, active forms.

INDUSTRIAL APPLICABILITY

As described hereinbefore, the present invention provides expression vectors overexpressing a target protein along with beta-lactamase. The expression vectors can produce in high levels a soluble, active form of heterogeneous target proteins in prokaryotic cells where the proteins are mostly expressed as inclusion bodies when other expression vectors are used.

The invention claimed is:

1. A method of producing an active, soluble target protein in a prokaryotic cell, comprising expressing the target protein and beta-lactamase as a first cistron and a second cistron, respectively, in a polycistron, wherein the polycistron is derived from a recombinant vector comprising (i) a promoter operable in the prokaryotic cell, (ii) a first cistron including a DNA sequence encoding the target protein and (iii) a second cistron including a DNA sequence encoding the beta-lactamase under conditions such that the target protein is produced in an active, soluble form.

2. The method according to claim 1, wherein the polycistron comprises in an operable manner in a 5' to 3' direction (i) a promoter operable in the prokaryotic cell, (ii) a first cistron including a DNA sequence encoding the target protein and (iii) a second cistron including a DNA sequence encoding beta-lactamase.

3. The method according to claim 1, wherein the polycistron is derived from from a recombinant vector comprising in an operable manner in a 5' to 3' direction (i) a promoter operable in the prokaryotic cell, (ii) a second cistron including a DNA sequence encoding beta-lactamase and (iii) a first cistron including a DNA sequence encoding the target protein.

4. The method according to claim 1, wherein the target protein is selected from the group consisting of human growth hormone, granulocyte-colony stimulating factor, interferon, basic fibroblast growth factor, insulin-like growth factor, keratinocyte growth factor, erythropoietin, thrombopoietin, human epidermal growth factor, platelet-derived growth factor, vascular endothelial growth factor, nerve growth factor, transforming growth factor, tumor necrosis factor, angiogenin, angiotensin and interleukin.

5. The method according to claim 4, wherein the target protein is selected from the group consisting of human growth hormone, granulocyte-colony stimulating factor, interferon-α2b, basic fibroblast growth factor, insulin-like growth factor-1, insulin-like growth factor-2 and keratinocyte growth factor.

6. The method according to claim 1, wherein the prokaryotic cell is Escherichia coli (E. coli).

7. The method according to claim 6, wherein the E. coli is selected from the group consisting of E. coli BL21 (DE3), E. coli BL21 Star (DE3) pLys S, E. coli HMS (DE3) and E. coli AD494 (DE3).

8. A polycistronic vector for expressing a target protein in an active, soluble form in a prokaryotic cell, comprising:
(i) a promoter operable in the prokaryotic cell;
(ii) a first cistron including a DNA sequence encoding the target protein; and
(iii) a second cistron including a DNA sequence encoding beta-lactamase.

9. The polycistronic vector according to claim 8, wherein the vector comprises in an operable manner in a 5' to 3' direction (i) a promoter operable in the prokaryotic cell, (ii) a first cistron including a DNA sequence encoding the target protein and (iii) a second cistron including a DNA sequence encoding beta-lactamase.

10. The polycistronic vector according to claim 8, wherein the vector comprises in an operable manner in a 5' to 3' direction (i) a promoter operable in the prokaryotic cell, (ii) a second cistron including a DNA sequence encoding beta-lactamase and (iii) a first cistron including a DNA sequence encoding the target protein.

11. The polycistronic vector according to claim 8, wherein the target protein is selected from the group consisting of human growth hormone, granulocyte-colony stimulating factor, interferon, basic fibroblast growth factor, insulin-like growth factor, keratinocyte growth factor, erythropoietin, thrombopoietin, human epidermal growth factor, platelet-derived growth factor, vascular endothelial growth factor, nerve growth factor, transforming growth factor, tumor necrosis factor, angiogenin, angiotensin and interleukin.

12. The polycistronic vector according to claim 11, wherein the target protein is selected from the group consisting of human growth hormone, granulocyte-colony stimulating factor, interferon-α2b, basic fibroblast growth factor, insulin-like growth factor-1, insulin-like growth factor-2 and keratinocyte growth factor.

13. The polycistronic vector according to claim 8, wherein the promoter is selected from the group consisting of T7, tac, trc, lac, lpp, phoA, recA, araBAD, proU, cst-1, tetA, cadA, nar, lpp-lac, starvation promoters, cspA, T7-lac operator, T3-lac operator, T5-lac operator, T4 gene 32 and nprM-lac operator.

14. The polycistronic vector according to claim 13, wherein the promoter is T7 promoter.

15. The polycistronic vector according to claim 8, wherein the vector is selected from the group consisting of pT0191, pT0-CSF, pT0-IFN, pT0-bFGF, pT0-IGF1, pT0-IGF2, pT0-KGF and pT0N-KFG.

16. A transformant transformed with the expression vector of claim 8.

17. The transformant according to claim 16, wherein the transformant is *Escherichia coli* (*E. coli*).

18. A method of producing an active, soluble target protein, comprising culturing the transformant of claim 17 and recovering an expressed target protein from a culture.

* * * * *

SEQUENCE LISTING

```
<160> NUMBER OF SEQ ID NOS: 26

<210> SEQ ID NO 1
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(30)

<400> SEQUENCE: 1 cat cat cat cat cat cat cat cat cat cac                          30
His His His His His His His His His His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2
```

```
His His His His His His His His His His
1               5                   10
```

```
<210> SEQ ID NO 3
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(15)

<400> SEQUENCE: 3 gac gac gac gac aaa                                          15
Asp Asp Asp Asp Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Asp Asp Asp Asp Lys
1               5

<210> SEQ ID NO 5
<211> LENGTH: 654
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (7)..(642)
<220> FEATURE:
<221> NAME/KEY: source
<222> LOCATION: (73)..(642)
<223> OTHER INFORMATION: Human growth hormone

<400> SEQUENCE: 5 aaacat atg ggc cat cat cat cat cat cat cat cat cac agc agc       48
       Met Gly His His His His His His His His His Ser Ser
        1               5                   10 gga tcc gac gac gac gac aaa ttc cca acc att ccc tta tcc agg ctt   96
Gly Ser Asp Asp Asp Asp Lys Phe Pro Thr Ile Pro Leu Ser Arg Leu
15                  20                  25                  30 ttt gac aac gct atg ctc cgc gcc cat cgt ctg cac cag ctg gcc ttt  144
Phe Asp Asn Ala Met Leu Arg Ala His Arg Leu His Gln Leu Ala Phe
                35                  40                  45 gac acc tac cag gag ttt gaa gaa gcc tat atc cca aag gaa cag aag  192
Asp Thr Tyr Gln Glu Phe Glu Glu Ala Tyr Ile Pro Lys Glu Gln Lys
            50                  55                  60 tat tca ttc ctg cag aac ccc cag acc tcc ctc tgt ttc tca gag tct  240
Tyr Ser Phe Leu Gln Asn Pro Gln Thr Ser Leu Cys Phe Ser Glu Ser
65                  70                  75 att ccg aca ccc tcc aac agg gag gaa aca caa cag aaa tcc aac cta  288
Ile Pro Thr Pro Ser Asn Arg Glu Glu Thr Gln Gln Lys Ser Asn Leu
            80                  85                  90 gag ctg ctc cgc atc tcc ctg ctg ctc atc cag tcg tgg ctg gag ccc  336
Glu Leu Leu Arg Ile Ser Leu Leu Leu Ile Gln Ser Trp Leu Glu Pro
95                  100                 105                 110 gtg cag ttc ctc agg agt gtc ttc gcc aac agc ctg gtg tac ggc gcc  384
```

```
Val Gln Phe Leu Arg Ser Val Phe Ala Asn Ser Leu Val Tyr Gly Ala
            115                 120                 125 tct gac agc aac gtc tat gac ctc cta aag gac cta gag gaa ggc atc     432
Ser Asp Ser Asn Val Tyr Asp Leu Leu Lys Asp Leu Glu Glu Gly Ile
            130                 135                 140 caa acg ctg atg ggg agg ctg gaa gat ggc agc ccc cgg act ggg cag     480
Gln Thr Leu Met Gly Arg Leu Glu Asp Gly Ser Pro Arg Thr Gly Gln
            145                 150                 155 atc ttc aag cag acc tac agc aag ttc gac aca aac tca cac aac gat     528
Ile Phe Lys Gln Thr Tyr Ser Lys Phe Asp Thr Asn Ser His Asn Asp
    160                 165                 170 gac gca cta ctc aag aac tac ggg ctg ctc tac tgc ttc agg aag gac     576
Asp Ala Leu Leu Lys Asn Tyr Gly Leu Leu Tyr Cys Phe Arg Lys Asp
175                 180                 185                 190 atg gac aag gtc gag aca ttc ctg cgc atc gtg cag tgc cgc tct gtg     624
Met Asp Lys Val Glu Thr Phe Leu Arg Ile Val Gln Cys Arg Ser Val
                195                 200                 205 gag ggc agc tgt ggc ttc taggtatact tt                               654
Glu Gly Ser Cys Gly Phe
            210

<210> SEQ ID NO 6
<211> LENGTH: 212
<212> TYPE: PRT
<213> ORGANISM: Artificial Sequence
<220> FEATURE:
<223> OTHER INFORMATION: Synthetic Construct

<400> SEQUENCE: 6

Met Gly His His His His His His His His Ser Ser Gly Ser
1               5                   10                  15

Asp Asp Asp Asp Lys Phe Pro Thr Ile Pro Leu Ser Arg Leu Phe Asp
            20                  25                  30

Asn Ala Met Leu Arg Ala His Arg Leu His Gln Leu Ala Phe Asp Thr
        35                  40                  45

Tyr Gln Glu Phe Glu Glu Ala Tyr Ile Pro Lys Glu Gln Lys Tyr Ser
    50                  55                  60

Phe Leu Gln Asn Pro Gln Thr Ser Leu Cys Phe Ser Glu Ser Ile Pro
65                  70                  75                  80

Thr Pro Ser Asn Arg Glu Glu Thr Gln Gln Lys Ser Asn Leu Glu Leu
                85                  90                  95

Leu Arg Ile Ser Leu Leu Leu Ile Gln Ser Trp Leu Glu Pro Val Gln
            100                 105                 110

Phe Leu Arg Ser Val Phe Ala Asn Ser Leu Val Tyr Gly Ala Ser Asp
        115                 120                 125

Ser Asn Val Tyr Asp Leu Leu Lys Asp Leu Glu Glu Gly Ile Gln Thr
    130                 135                 140

Leu Met Gly Arg Leu Glu Asp Gly Ser Pro Arg Thr Gly Gln Ile Phe
145                 150                 155                 160

Lys Gln Thr Tyr Ser Lys Phe Asp Thr Asn Ser His Asn Asp Ala
                165                 170                 175

Leu Leu Lys Asn Tyr Gly Leu Leu Tyr Cys Phe Arg Lys Asp Met Asp
            180                 185                 190

Lys Val Glu Thr Phe Leu Arg Ile Val Gln Cys Arg Ser Val Glu Gly
        195                 200                 205

Ser Cys Gly Phe
    210
```

```
<210> SEQ ID NO 7
<211> LENGTH: 588
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (7)..(579)
<220> FEATURE:
<221> NAME/KEY: source
<222> LOCATION: (58)..(579)
<223> OTHER INFORMATION: Human granulocyte colony stimulating factor

<400> SEQUENCE: 7 aaacat atg ggc cat cat cat cat cat cat cat cat cac gac gac        48
       Met Gly His His His His His His His His Asp Asp
       1               5                   10 gac gac aaa act cca tta ggt cca gcc agc tcc ctt ccc caa agc ttc    96
Asp Asp Lys Thr Pro Leu Gly Pro Ala Ser Ser Leu Pro Gln Ser Phe
15                  20                  25                  30 ctg ctc aag tgc tta gag caa gtg agg agg atc cag ggc gat ggc gca   144
Leu Leu Lys Cys Leu Glu Gln Val Arg Arg Ile Gln Gly Asp Gly Ala
                35                  40                  45 gcg ctc cag gag aag ctg tgt gcc acc tac aag ctg tgc cac ccc gag   192
Ala Leu Gln Glu Lys Leu Cys Ala Thr Tyr Lys Leu Cys His Pro Glu
        50                  55                  60 gag ctg gtg ctg ctc gga cac tct ctg ggc atc ccc tgg gct ccc ctg   240
Glu Leu Val Leu Leu Gly His Ser Leu Gly Ile Pro Trp Ala Pro Leu
65                  70                  75 agc agc tgc ccc agc cag gcc ctg cag ctg gca ggc tgc ttg agc caa   288
Ser Ser Cys Pro Ser Gln Ala Leu Gln Leu Ala Gly Cys Leu Ser Gln
80                  85                  90 ctc cat agc ggc ctt ttc ctc tac cag ggg ctc ctg cag gcc ctg gaa   336
Leu His Ser Gly Leu Phe Leu Tyr Gln Gly Leu Leu Gln Ala Leu Glu
95                  100                 105                 110 ggg atc tcc ccc gag ttg ggt ccc acc ttg gac aca ctg cag ctg gac   384
Gly Ile Ser Pro Glu Leu Gly Pro Thr Leu Asp Thr Leu Gln Leu Asp
                115                 120                 125 gtc gcc gac ttt gcc acc acc atc tgg cag cag atg gaa gaa ctg gga   432
Val Ala Asp Phe Ala Thr Thr Ile Trp Gln Gln Met Glu Glu Leu Gly
        130                 135                 140 atg gcc cct gcc ctg cag ccc acc cag ggt gcc atg ccg gcc ttc gcc   480
Met Ala Pro Ala Leu Gln Pro Thr Gln Gly Ala Met Pro Ala Phe Ala
145                 150                 155 tct gct ttc cag cgc cgg gca gga ggg gtc cta gtt gcc tcc cat ctg   528
Ser Ala Phe Gln Arg Arg Ala Gly Gly Val Leu Val Ala Ser His Leu
160                 165                 170 cag agc ttc ctg gag gtg tcg tac cgc gtt cta cgc cac ctt gcg cag   576
Gln Ser Phe Leu Glu Val Ser Tyr Arg Val Leu Arg His Leu Ala Gln
175                 180                 185                 190 ccc taaaagctt                                                      588
Pro

<210> SEQ ID NO 8
<211> LENGTH: 191
<212> TYPE: PRT
<213> ORGANISM: Artificial Sequence
<220> FEATURE:
<223> OTHER INFORMATION: Synthetic Construct

<400> SEQUENCE: 8

Met Gly His His His His His His His His Asp Asp Asp Asp
```

```
              1               5                  10                 15
Lys Thr Pro Leu Gly Pro Ala Ser Ser Leu Pro Gln Ser Phe Leu Leu
             20                  25                 30

Lys Cys Leu Glu Gln Val Arg Arg Ile Gln Gly Asp Gly Ala Ala Leu
             35                  40                 45

Gln Glu Lys Leu Cys Ala Thr Tyr Lys Leu Cys His Pro Glu Glu Leu
             50                  55                 60

Val Leu Leu Gly His Ser Leu Gly Ile Pro Trp Ala Pro Leu Ser Ser
 65                  70                 75                 80

Cys Pro Ser Gln Ala Leu Gln Leu Ala Gly Cys Leu Ser Gln Leu His
             85                  90                 95

Ser Gly Leu Phe Leu Tyr Gln Gly Leu Leu Gln Ala Leu Glu Gly Ile
            100                 105                110

Ser Pro Glu Leu Gly Pro Thr Leu Asp Thr Leu Gln Leu Asp Val Ala
            115                 120                125

Asp Phe Ala Thr Thr Ile Trp Gln Gln Met Glu Glu Leu Gly Met Ala
            130                 135                140

Pro Ala Leu Gln Pro Thr Gln Gly Ala Met Pro Ala Phe Ala Ser Ala
145                 150                 155                160

Phe Gln Arg Arg Ala Gly Gly Val Leu Val Ala Ser His Leu Gln Ser
            165                 170                175

Phe Leu Glu Val Ser Tyr Arg Val Leu Arg His Leu Ala Gln Pro
            180                 185                190
```

<210> SEQ ID NO 9
<211> LENGTH: 561
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (7)..(552)
<220> FEATURE:
<221> NAME/KEY: source
<222> LOCATION: (58)..(552)
<223> OTHER INFORMATION: Human interferon alpha 2b

<400> SEQUENCE: 9

```
aaacat atg ggc cat cat cat cat cat cat cat cat cac gac gac           48
       Met Gly His His His His His His His His Asp Asp
        1               5                  10 gac gac aaa tgt gat ctg cct caa acc cac agc ctg ggt agc agg agg      96
Asp Asp Lys Cys Asp Leu Pro Gln Thr His Ser Leu Gly Ser Arg Arg
 15                  20                  25                  30 acc ttg atg ctc ctg gca cag atg agg aga atc tct ctt ttc tcc tgc    144
Thr Leu Met Leu Leu Ala Gln Met Arg Arg Ile Ser Leu Phe Ser Cys
                 35                  40                  45 ttg aag gac aga cat gac ttt gga ttt ccc cag gag gag ttt ggc aac    192
Leu Lys Asp Arg His Asp Phe Gly Phe Pro Gln Glu Glu Phe Gly Asn
             50                  55                  60 cag ttc caa aag gct gaa acc atc cct gtc ctc cat gag atg atc cag    240
Gln Phe Gln Lys Ala Glu Thr Ile Pro Val Leu His Glu Met Ile Gln
             65                  70                  75 cag atc ttc aat ctc ttc agc aca aag gac tca tct gct gct tgg gat    288
Gln Ile Phe Asn Leu Phe Ser Thr Lys Asp Ser Ser Ala Ala Trp Asp
         80                  85                  90 gag acc ctc cta gac aaa ttc tac act gaa ctc tac cag cag ctg aat    336
Glu Thr Leu Leu Asp Lys Phe Tyr Thr Glu Leu Tyr Gln Gln Leu Asn
 95                 100                 105                 110
```

```
gac ctg gaa gcc tgt gtg ata cag ggg gtg ggg gtg aca gag act ccc      384
Asp Leu Glu Ala Cys Val Ile Gln Gly Val Gly Val Thr Glu Thr Pro
            115                 120                 125 ctg atg aag gag gac tcc att ctg gct gtg agg aaa tac ttc caa aga      432
Leu Met Lys Glu Asp Ser Ile Leu Ala Val Arg Lys Tyr Phe Gln Arg
130                 135                 140 atc act ctc tat ctg aaa gag aag aaa tac agc cct tgt gcc tgg gag      480
Ile Thr Leu Tyr Leu Lys Glu Lys Lys Tyr Ser Pro Cys Ala Trp Glu
                145                 150                 155 gtt gtc aga gca gaa atc atg aga tct ttt tct ttg tca aca aac ttg      528
Val Val Arg Ala Glu Ile Met Arg Ser Phe Ser Leu Ser Thr Asn Leu
160                 165                 170 caa gaa agt tta aga agt aag gaa tgaaagctt                            561
Gln Glu Ser Leu Arg Ser Lys Glu
175                 180
```

```
<210> SEQ ID NO 10
<211> LENGTH: 182
<212> TYPE: PRT
<213> ORGANISM: Artificial Sequence
<220> FEATURE:
<223> OTHER INFORMATION: Synthetic Construct

<400> SEQUENCE: 10

Met Gly His His His His His His His His Asp Asp Asp Asp
1               5                   10                  15

Lys Cys Asp Leu Pro Gln Thr His Ser Leu Gly Ser Arg Arg Thr Leu
                20                  25                  30

Met Leu Leu Ala Gln Met Arg Arg Ile Ser Leu Phe Ser Cys Leu Lys
            35                  40                  45

Asp Arg His Asp Phe Gly Phe Pro Gln Glu Glu Phe Gly Asn Gln Phe
        50                  55                  60

Gln Lys Ala Glu Thr Ile Pro Val Leu His Glu Met Ile Gln Gln Ile
65                  70                  75                  80

Phe Asn Leu Phe Ser Thr Lys Asp Ser Ser Ala Ala Trp Asp Glu Thr
                85                  90                  95

Leu Leu Asp Lys Phe Tyr Thr Glu Leu Tyr Gln Gln Leu Asn Asp Leu
            100                 105                 110

Glu Ala Cys Val Ile Gln Gly Val Gly Val Thr Glu Thr Pro Leu Met
        115                 120                 125

Lys Glu Asp Ser Ile Leu Ala Val Arg Lys Tyr Phe Gln Arg Ile Thr
130                 135                 140

Leu Tyr Leu Lys Glu Lys Lys Tyr Ser Pro Cys Ala Trp Glu Val Val
145                 150                 155                 160

Arg Ala Glu Ile Met Arg Ser Phe Ser Leu Ser Thr Asn Leu Gln Glu
                165                 170                 175

Ser Leu Arg Ser Lys Glu
            180
```

```
<210> SEQ ID NO 11
<211> LENGTH: 531
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (7)..(522)
<220> FEATURE:
<221> NAME/KEY: source
```

<222> LOCATION: (58)..(522)
<223> OTHER INFORMATION: Human basic fibroblast growth factor

<400> SEQUENCE: 11

```
aaacat atg ggc cat cat cat cat cat cat cat cat cac gac gac        48
       Met Gly His His His His His His His His Asp Asp
       1               5                   10 gac gac aaa atg gca gcc ggt agc atc acc acg ctg ccg gcc ctg ccg   96
Asp Asp Lys Met Ala Ala Gly Ser Ile Thr Thr Leu Pro Ala Leu Pro
15                  20                  25                  30 gag gat ggc ggc agc ggc gcc ttc ccg ccg ggc cac ttc aag gac ccg   144
Glu Asp Gly Gly Ser Gly Ala Phe Pro Pro Gly His Phe Lys Asp Pro
                35                  40                  45 aag cgt ctg tac tgc aag aac ggt ggc ttc ttc ctg cgc atc cac ccg   192
Lys Arg Leu Tyr Cys Lys Asn Gly Gly Phe Phe Leu Arg Ile His Pro
        50                  55                  60 gac ggc cgt gtt gac ggt gtc cgt gag aag agc gac cct cac atc aag   240
Asp Gly Arg Val Asp Gly Val Arg Glu Lys Ser Asp Pro His Ile Lys
65                  70                  75 ctg caa ctg caa gca gaa gag cgt ggt gtt gtg tct atc aaa ggt gtg   288
Leu Gln Leu Gln Ala Glu Glu Arg Gly Val Val Ser Ile Lys Gly Val
80                  85                  90 tgt gct aac cgt tac ctg gct atg aag gaa gat ggt cgt ctg ctg gct   336
Cys Ala Asn Arg Tyr Leu Ala Met Lys Glu Asp Gly Arg Leu Leu Ala
95                  100                 105                 110 tct aaa tgt gtt acg gat gag tgt ttc ttc ttc gaa cgt ctg gaa tct   384
Ser Lys Cys Val Thr Asp Glu Cys Phe Phe Phe Glu Arg Leu Glu Ser
                115                 120                 125 aat aac tac aat act tac cgt tcc cgt aaa tac acc agc tgg tat gtg   432
Asn Asn Tyr Asn Thr Tyr Arg Ser Arg Lys Tyr Thr Ser Trp Tyr Val
        130                 135                 140 gca ctg aaa cgt act ggt cag tat aaa ctg ggt tcc aaa acc ggt cct   480
Ala Leu Lys Arg Thr Gly Gln Tyr Lys Leu Gly Ser Lys Thr Gly Pro
                145                 150                 155 ggt cag aaa gct atc ctg ttt ctg cca atg tct gct aag agc taaaagctt 531
Gly Gln Lys Ala Ile Leu Phe Leu Pro Met Ser Ala Lys Ser
        160                 165                 170
```

<210> SEQ ID NO 12
<211> LENGTH: 172
<212> TYPE: PRT
<213> ORGANISM: Artificial Sequence
<220> FEATURE:
<223> OTHER INFORMATION: Synthetic Construct

<400> SEQUENCE: 12

```
Met Gly His His His His His His His His Asp Asp Asp
1               5                   10                  15

Lys Met Ala Ala Gly Ser Ile Thr Thr Leu Pro Ala Leu Pro Glu Asp
                20                  25                  30

Gly Gly Ser Gly Ala Phe Pro Pro Gly His Phe Lys Asp Pro Lys Arg
            35                  40                  45

Leu Tyr Cys Lys Asn Gly Gly Phe Phe Leu Arg Ile His Pro Asp Gly
        50                  55                  60

Arg Val Asp Gly Val Arg Glu Lys Ser Asp Pro His Ile Lys Leu Gln
65                  70                  75                  80

Leu Gln Ala Glu Glu Arg Gly Val Val Ser Ile Lys Gly Val Cys Ala
                85                  90                  95

Asn Arg Tyr Leu Ala Met Lys Glu Asp Gly Arg Leu Leu Ala Ser Lys
            100                 105                 110
```

```
Cys Val Thr Asp Glu Cys Phe Phe Glu Arg Leu Glu Ser Asn Asn
        115                 120                 125
Tyr Asn Thr Tyr Arg Ser Arg Lys Tyr Thr Ser Trp Tyr Val Ala Leu
    130                 135                 140
Lys Arg Thr Gly Gln Tyr Lys Leu Gly Ser Lys Thr Gly Pro Gly Gln
145                 150                 155                 160
Lys Ala Ile Leu Phe Leu Pro Met Ser Ala Lys Ser
            165                 170

<210> SEQ ID NO 13
<211> LENGTH: 279
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (7)..(267)
<220> FEATURE:
<221> NAME/KEY: source
<222> LOCATION: (58)..(267)
<223> OTHER INFORMATION: Human insulin like growth factor-1

<400> SEQUENCE: 13 aaacat atg ggc cat cat cat cat cat cat cat cat cac gac gac        48
       Met Gly His His His His His His His His Asp Asp
        1               5                   10 gac gac aaa ggt ccg gaa acc ctg tgc ggc gct gag ctg gtt gac gct   96
Asp Asp Lys Gly Pro Glu Thr Leu Cys Gly Ala Glu Leu Val Asp Ala
15                  20                  25                  30 ctg caa ttc gtt tgc ggt gac cgt ggt ttc tac ttc aac aaa ccg act  144
Leu Gln Phe Val Cys Gly Asp Arg Gly Phe Tyr Phe Asn Lys Pro Thr
                35                  40                  45 ggt tac ggt tcc tct tct cgt cgt gct ccg cag acc ggt atc gtt gac  192
Gly Tyr Gly Ser Ser Ser Arg Arg Ala Pro Gln Thr Gly Ile Val Asp
            50                  55                  60 gaa tgc tgc ttc cgt tct tgc gac ctg cgt cgt ctg gaa atg tac tgc  240
Glu Cys Cys Phe Arg Ser Cys Asp Leu Arg Arg Leu Glu Met Tyr Cys
65                  70                  75 gct ccg ctg aaa ccg gcg aag tct gct taatgaaagc tt                279
Ala Pro Leu Lys Pro Ala Lys Ser Ala
        80                  85

<210> SEQ ID NO 14
<211> LENGTH: 87
<212> TYPE: PRT
<213> ORGANISM: Artificial Sequence
<220> FEATURE:
<223> OTHER INFORMATION: Synthetic Construct

<400> SEQUENCE: 14

Met Gly His His His His His His His His Asp Asp Asp Asp
1               5                   10                  15

Lys Gly Pro Glu Thr Leu Cys Gly Ala Glu Leu Val Asp Ala Leu Gln
                20                  25                  30

Phe Val Cys Gly Asp Arg Gly Phe Tyr Phe Asn Lys Pro Thr Gly Tyr
            35                  40                  45

Gly Ser Ser Ser Arg Arg Ala Pro Gln Thr Gly Ile Val Asp Glu Cys
        50                  55                  60

Cys Phe Arg Ser Cys Asp Leu Arg Arg Leu Glu Met Tyr Cys Ala Pro
65                  70                  75                  80
```

<210> SEQ ID NO 15
<211> LENGTH: 267
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (7)..(258)
<220> FEATURE:
<221> NAME/KEY: source
<222> LOCATION: (58)..(258)
<223> OTHER INFORMATION: Human insulin like growth factor-2

<400> SEQUENCE: 15

```
aaacat atg ggc cat cat cat cat cat cat cat cat cac gac gac         48
       Met Gly His His His His His His His His Asp Asp
       1               5                  10 gac gac aaa gct tac cgc ccg agc gag acc ctg tgc ggc ggt gag ctg    96
Asp Asp Lys Ala Tyr Arg Pro Ser Glu Thr Leu Cys Gly Gly Glu Leu
15                  20                  25                  30 gtg gac acc ctc cag ttc gtc tgt ggt gac cgc ggc ttc tac ttc agc   144
Val Asp Thr Leu Gln Phe Val Cys Gly Asp Arg Gly Phe Tyr Phe Ser
                35                  40                  45 cgt ccg gca agc cgt gtg agc cgt cgc agc cgt ggc atc gtt gag gag   192
Arg Pro Ala Ser Arg Val Ser Arg Arg Ser Arg Gly Ile Val Glu Glu
            50                  55                  60 tgc tgt ttc cgc agc tgt gac ctg gcc ctc ctg gag acg tac tgt gct   240
Cys Cys Phe Arg Ser Cys Asp Leu Ala Leu Leu Glu Thr Tyr Cys Ala
65                  70                  75 acc ccg gcc aag tcc gag taaaagctt                                  267
Thr Pro Ala Lys Ser Glu
        80
```

<210> SEQ ID NO 16
<211> LENGTH: 84
<212> TYPE: PRT
<213> ORGANISM: Artificial Sequence
<220> FEATURE:
<223> OTHER INFORMATION: Synthetic Construct

<400> SEQUENCE: 16

```
Met Gly His His His His His His His His Asp Asp Asp
1               5                  10                  15

Lys Ala Tyr Arg Pro Ser Glu Thr Leu Cys Gly Gly Glu Leu Val Asp
                20                  25                  30

Thr Leu Gln Phe Val Cys Gly Asp Arg Gly Phe Tyr Phe Ser Arg Pro
            35                  40                  45

Ala Ser Arg Val Ser Arg Arg Ser Arg Gly Ile Val Glu Glu Cys Cys
        50                  55                  60

Phe Arg Ser Cys Asp Leu Ala Leu Leu Glu Thr Tyr Cys Ala Thr Pro
65                  70                  75                  80

Ala Lys Ser Glu
```

<210> SEQ ID NO 17
<211> LENGTH: 861
<212> TYPE: DNA
<213> ORGANISM: Artificial Sequence
<220> FEATURE:
<223> OTHER INFORMATION: Synthetic
<220> FEATURE:

<221> NAME/KEY: CDS
<222> LOCATION: (1)..(858)

<400> SEQUENCE: 17

```
atg agt att caa cat ttc cgt gtc gcc ctt att ccc ttt ttt gcg gca      48
Met Ser Ile Gln His Phe Arg Val Ala Leu Ile Pro Phe Phe Ala Ala
1               5                   10                  15 ttt tgc ctt cct gtt ttt gct cac cca gaa acg ctg gtg aaa gta aaa      96
Phe Cys Leu Pro Val Phe Ala His Pro Glu Thr Leu Val Lys Val Lys
            20                  25                  30 gat gct gaa gat cag ttg ggt gca cga gtg ggt tac atc gaa ctg gat     144
Asp Ala Glu Asp Gln Leu Gly Ala Arg Val Gly Tyr Ile Glu Leu Asp
        35                  40                  45 ctc aac agc ggt aag atc ctt gag agt ttt cgc ccc gaa gaa cgt ttt     192
Leu Asn Ser Gly Lys Ile Leu Glu Ser Phe Arg Pro Glu Glu Arg Phe
50                  55                  60 cca atg atg agc act ttt aaa gtt ctg cta tgt ggc gcg gta tta tcc     240
Pro Met Met Ser Thr Phe Lys Val Leu Leu Cys Gly Ala Val Leu Ser
65                  70                  75                  80 cgt gtt gac gcc ggg caa gag caa ctc ggt cgc cgc ata cac tat tct     288
Arg Val Asp Ala Gly Gln Glu Gln Leu Gly Arg Arg Ile His Tyr Ser
                85                  90                  95 cag aat gac ttg gtt gag tac tca cca gtc aca gaa aag cat ctt acg     336
Gln Asn Asp Leu Val Glu Tyr Ser Pro Val Thr Glu Lys His Leu Thr
            100                 105                 110 gat ggc atg aca gta aga gaa tta tgc agt gct gcc ata acc atg agt     384
Asp Gly Met Thr Val Arg Glu Leu Cys Ser Ala Ala Ile Thr Met Ser
        115                 120                 125 gat aac act gcg gcc aac tta ctt ctg aca acg atc gga gga ccg aag     432
Asp Asn Thr Ala Ala Asn Leu Leu Leu Thr Thr Ile Gly Gly Pro Lys
    130                 135                 140 gag cta acc gct ttt ttg cac aac atg ggg gat cat gta act cgc ctt     480
Glu Leu Thr Ala Phe Leu His Asn Met Gly Asp His Val Thr Arg Leu
145                 150                 155                 160 gat cgt tgg gaa ccg gag ctg aat gaa gcc ata cca aac gac gag cgt     528
Asp Arg Trp Glu Pro Glu Leu Asn Glu Ala Ile Pro Asn Asp Glu Arg
                165                 170                 175 gac acc acg atg cct gca gca atg gca aca acg ttg cgc aaa cta tta     576
Asp Thr Thr Met Pro Ala Ala Met Ala Thr Thr Leu Arg Lys Leu Leu
            180                 185                 190 act ggc gaa cta ctt act cta gct tcc cgg caa caa tta ata gac tgg     624
Thr Gly Glu Leu Leu Thr Leu Ala Ser Arg Gln Gln Leu Ile Asp Trp
        195                 200                 205 atg gag gcg gat aaa gtt gca gga cca ctt ctg cgc tcg gcc ctt ccg     672
Met Glu Ala Asp Lys Val Ala Gly Pro Leu Leu Arg Ser Ala Leu Pro
    210                 215                 220 gct ggc tgg ttt att gct gat aaa tct gga gcc ggt gag cgt ggg tct     720
Ala Gly Trp Phe Ile Ala Asp Lys Ser Gly Ala Gly Glu Arg Gly Ser
225                 230                 235                 240 cgc ggt atc att gca gca ctg ggg cca gat ggt aag ccc tcc cgt atc     768
Arg Gly Ile Ile Ala Ala Leu Gly Pro Asp Gly Lys Pro Ser Arg Ile
                245                 250                 255 gta gtt atc tac acg acg ggg agt cag gca act atg gat gaa cga aat     816
Val Val Ile Tyr Thr Thr Gly Ser Gln Ala Thr Met Asp Glu Arg Asn
            260                 265                 270 aga cag atc gct gag ata ggt gcc tca ctg att aag cat tgg taa         861
Arg Gln Ile Ala Glu Ile Gly Ala Ser Leu Ile Lys His Trp
        275                 280                 285
```

<210> SEQ ID NO 18

```
<211> LENGTH: 286
<212> TYPE: PRT
<213> ORGANISM: Artificial Sequence
<220> FEATURE:
<223> OTHER INFORMATION: Synthetic Construct

<400> SEQUENCE: 18

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 19
<211> LENGTH: 42
<212> TYPE: DNA
<213> ORGANISM: Artificial Sequence
<220> FEATURE:
<223> OTHER INFORMATION: Synthetic

<400> SEQUENCE: 19
aaacatatgg gccatcatca tcatcatcat catcatcatc ac                    42
```

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
aaaaagcttt tactagaagc cacagctgcc    30

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
aaaaagctta aggagatggc gccca    25

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
aaagcatgcc tagaagccac agctg    25

<210> SEQ ID NO 23
<211> LENGTH: 555
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(546)
<220> FEATURE:
<221> NAME/KEY: source
<222> LOCATION: (58)..(546)
<223> OTHER INFORMATION: Human keratinocyte growth factor

<400> SEQUENCE: 23

```
aaa cat atg ggc cat cat cat cat cat cat cat cat cac gac gac      48
Lys His Met Gly His His His His His His His His Asp Asp
1               5                  10                 15 gac gac aaa tgc aat gac atg act cca gag caa atg gct acc aat gtg  96
Asp Asp Lys Cys Asn Asp Met Thr Pro Glu Gln Met Ala Thr Asn Val
            20                  25                  30 aac tgt tcc agc cct gag cgt cac acc cgt agc tat gat tac atg gaa  144
Asn Cys Ser Ser Pro Glu Arg His Thr Arg Ser Tyr Asp Tyr Met Glu
        35                  40                  45 ggt ggt gat atc cgt gtg cgt cgt ctc ttc tgt cgt acc cag tgg tat  192
Gly Gly Asp Ile Arg Val Arg Arg Leu Phe Cys Arg Thr Gln Trp Tyr
    50                  55                  60 ctg cgt atc gat aaa cgt ggc aaa gta aaa ggc acc caa gag atg aag  240
Leu Arg Ile Asp Lys Arg Gly Lys Val Lys Gly Thr Gln Glu Met Lys
65                  70                  75                  80
```

```
aat aat tac aat atc atg gaa atc cgt acc gtg gca gtt ggt att gtg    288
Asn Asn Tyr Asn Ile Met Glu Ile Arg Thr Val Ala Val Gly Ile Val
            85                  90                  95 gca atc aaa ggt gtg gaa agc gag ttc tat ctg gca atg aac aag gaa    336
Ala Ile Lys Gly Val Glu Ser Glu Phe Tyr Leu Ala Met Asn Lys Glu
            100                 105                 110 ggt aaa ctc tat gca aag aaa gaa tgc aat gaa gat tgt aac ttc aaa    384
Gly Lys Leu Tyr Ala Lys Lys Glu Cys Asn Glu Asp Cys Asn Phe Lys
        115                 120                 125 gaa ctg att ctg gaa aac cat tac aac acc tat gca tct gct aaa tgg    432
Glu Leu Ile Leu Glu Asn His Tyr Asn Thr Tyr Ala Ser Ala Lys Trp
    130                 135                 140 acc cac aac ggt ggt gaa atg ttt gtt gcc ctg aat caa aag ggt att    480
Thr His Asn Gly Gly Glu Met Phe Val Ala Leu Asn Gln Lys Gly Ile
145                 150                 155                 160 cct gta cgt ggt aag aag acg aag aaa gaa cag aaa acc gcc cac ttt    528
Pro Val Arg Gly Lys Lys Thr Lys Lys Glu Gln Lys Thr Ala His Phe
                165                 170                 175 ctg cct atg gca atc act taaaagctt                                  555
Leu Pro Met Ala Ile Thr
            180

<210> SEQ ID NO 24
<211> LENGTH: 182
<212> TYPE: PRT
<213> ORGANISM: Artificial Sequence
<220> FEATURE:
<223> OTHER INFORMATION: Synthetic Construct

<400> SEQUENCE: 24

Lys His Met Gly His His His His His His His His Asp Asp
1               5                   10                  15

Asp Asp Lys Cys Asn Asp Met Thr Pro Glu Gln Met Ala Thr Asn Val
            20                  25                  30

Asn Cys Ser Ser Pro Glu Arg His Thr Arg Ser Tyr Asp Tyr Met Glu
        35                  40                  45

Gly Gly Asp Ile Arg Val Arg Arg Leu Phe Cys Arg Thr Gln Trp Tyr
    50                  55                  60

Leu Arg Ile Asp Lys Arg Gly Lys Val Lys Gly Thr Gln Glu Met Lys
65                  70                  75                  80

Asn Asn Tyr Asn Ile Met Glu Ile Arg Thr Val Ala Val Gly Ile Val
            85                  90                  95

Ala Ile Lys Gly Val Glu Ser Glu Phe Tyr Leu Ala Met Asn Lys Glu
            100                 105                 110

Gly Lys Leu Tyr Ala Lys Lys Glu Cys Asn Glu Asp Cys Asn Phe Lys
        115                 120                 125

Glu Leu Ile Leu Glu Asn His Tyr Asn Thr Tyr Ala Ser Ala Lys Trp
    130                 135                 140

Thr His Asn Gly Gly Glu Met Phe Val Ala Leu Asn Gln Lys Gly Ile
145                 150                 155                 160

Pro Val Arg Gly Lys Lys Thr Lys Lys Glu Gln Lys Thr Ala His Phe
                165                 170                 175

Leu Pro Met Ala Ile Thr
            180
```

<210> SEQ ID NO 25
<211> LENGTH: 507
<212> TYPE: DNA
<213> ORGANISM: Homo sapiens
<220> FEATURE:
<221> NAME/KEY: CDS
<222> LOCATION: (1)..(498)
<223> OTHER INFORMATION: Human keratinocyte growth factor

<400> SEQUENCE: 25

```
aaa cat atg tgc aat gac atg act cca gag caa atg gct acc aat gtg        48
Lys His Met Cys Asn Asp Met Thr Pro Glu Gln Met Ala Thr Asn Val
1               5                  10                  15 aac tgt tcc agc cct gag cgt cac acc cgt agc tat gat tac atg gaa        96
Asn Cys Ser Ser Pro Glu Arg His Thr Arg Ser Tyr Asp Tyr Met Glu
            20                  25                  30 ggt ggt gat atc cgt gtg cgt cgt ctc ttc tgt cgt acc cag tgg tat       144
Gly Gly Asp Ile Arg Val Arg Arg Leu Phe Cys Arg Thr Gln Trp Tyr
        35                  40                  45 ctg cgt atc gat aaa cgt ggc aaa gta aaa ggc acc caa gag atg aag       192
Leu Arg Ile Asp Lys Arg Gly Lys Val Lys Gly Thr Gln Glu Met Lys
    50                  55                  60 aat aat tac aat atc atg gaa atc cgt acc gtg gca gtt ggt att gtg       240
Asn Asn Tyr Asn Ile Met Glu Ile Arg Thr Val Ala Val Gly Ile Val
65                  70                  75                  80 gca atc aaa ggt gtg gaa agc gag ttc tat ctg gca atg aac aag gaa       288
Ala Ile Lys Gly Val Glu Ser Glu Phe Tyr Leu Ala Met Asn Lys Glu
                85                  90                  95 ggt aaa ctc tat gca aag aaa gaa tgc aat gaa gat tgt aac ttc aaa       336
Gly Lys Leu Tyr Ala Lys Lys Glu Cys Asn Glu Asp Cys Asn Phe Lys
            100                 105                 110 gaa ctg att ctg gaa aac cat tac aac acc tat gca tct gct aaa tgg       384
Glu Leu Ile Leu Glu Asn His Tyr Asn Thr Tyr Ala Ser Ala Lys Trp
        115                 120                 125 acc cac aac ggt ggt gaa atg ttt gtt gcc ctg aat caa aag ggt att       432
Thr His Asn Gly Gly Glu Met Phe Val Ala Leu Asn Gln Lys Gly Ile
    130                 135                 140 cct gta cgt ggt aag aag acg aag aaa gaa cag aaa acc gcc cac ttt       480
Pro Val Arg Gly Lys Lys Thr Lys Lys Glu Gln Lys Thr Ala His Phe
145                 150                 155                 160 ctg cct atg gca atc act taaaagctt                                     507
Leu Pro Met Ala Ile Thr
                165
```

<210> SEQ ID NO 26
<211> LENGTH: 166
<212> TYPE: PRT
<213> ORGANISM: Homo sapiens

<400> SEQUENCE: 26

```
Lys His Met Cys Asn Asp Met Thr Pro Glu Gln Met Ala Thr Asn Val
1               5                  10                  15

Asn Cys Ser Ser Pro Glu Arg His Thr Arg Ser Tyr Asp Tyr Met Glu
            20                  25                  30

Gly Gly Asp Ile Arg Val Arg Arg Leu Phe Cys Arg Thr Gln Trp Tyr
        35                  40                  45

Leu Arg Ile Asp Lys Arg Gly Lys Val Lys Gly Thr Gln Glu Met Lys
    50                  55                  60

Asn Asn Tyr Asn Ile Met Glu Ile Arg Thr Val Ala Val Gly Ile Val
65                  70                  75                  80
```

-continued

```
Ala Ile Lys Gly Val Glu Ser Glu Phe Tyr Leu Ala Met Asn Lys Glu
             85                  90                  95

Gly Lys Leu Tyr Ala Lys Lys Glu Cys Asn Glu Asp Cys Asn Phe Lys
            100             105             110

Glu Leu Ile Leu Glu Asn His Tyr Asn Thr Tyr Ala Ser Ala Lys Trp
        115             120             125

Thr His Asn Gly Gly Glu Met Phe Val Ala Leu Asn Gln Lys Gly Ile
        130             135             140

Pro Val Arg Gly Lys Lys Thr Lys Lys Glu Gln Lys Thr Ala His Phe
145             150             155             160

Leu Pro Met Ala Ile Thr
                165
```